United States Patent [19]
Chow et al.

[11] Patent Number: 6,149,787
[45] Date of Patent: Nov. 21, 2000

[54] EXTERNAL MATERIAL ACCESSION SYSTEMS AND METHODS

[75] Inventors: Andrea W. Chow, Los Altos; Robert S. Dubrow, San Carlos; J. Wallace Parce, Palo Alto; Steven A. Sundberg, San Francisco; Jeffrey A. Wolk, Half Moon Bay, all of Calif.

[73] Assignee: Caliper Technologies Corp., Mountain View, Calif.

[21] Appl. No.: 09/173,469

[22] Filed: Oct. 14, 1998

[51] Int. Cl.[7] .................................................. G01N 27/26
[52] U.S. Cl. .......................... 204/451; 204/453; 204/601; 204/604; 73/864.02; 73/864.22; 436/180; 422/99; 422/100
[58] Field of Search ........................... 73/864.01, 864.02, 73/864.22, 864.11, 864.12, 863.32; 436/180; 29/428; 422/99, 100; 204/451, 454, 601, 604, 453

[56] References Cited

U.S. PATENT DOCUMENTS

| | | |
|---|---|---|
| 4,390,403 | 6/1983 | Batchelder . |
| 4,457,184 | 7/1984 | Shiono ................................ 73/864.11 |
| 4,908,112 | 3/1990 | Pace . |
| 5,126,022 | 6/1992 | Soane et al. . |
| 5,229,297 | 7/1993 | Schnipelsky et al. .................... 436/94 |
| 5,282,942 | 2/1994 | Herrick et al. . |
| 5,286,356 | 2/1994 | Jones et al. .......................... 204/182.8 |
| 5,358,612 | 10/1994 | Dasgupta et al. . |
| 5,415,747 | 5/1995 | Holloway . |
| 5,498,392 | 3/1996 | Wilding et al. . |
| 5,571,410 | 11/1996 | Swedberg et al. . |
| 5,585,069 | 12/1996 | Zanzucchi et al. . |
| 5,593,838 | 1/1997 | Zanzucchi et al. . |
| 5,603,351 | 2/1997 | Cherukuri et al. . |
| 5,635,358 | 6/1997 | Wilding et al. . |
| 5,637,469 | 6/1997 | Wilding et al. . |
| 5,750,015 | 5/1998 | Soane et al. . |
| 5,779,868 | 7/1998 | Parce et al. ............................ 204/604 |
| 5,800,690 | 9/1998 | Chow et al. ............................ 204/451 |
| 5,890,745 | 4/1999 | Kovacs . |
| 5,980,704 | 11/1999 | Cherukuri et al. ...................... 204/269 |

FOREIGN PATENT DOCUMENTS

| | | |
|---|---|---|
| 402181632A | 7/1990 | Japan . |
| WO 9604547 | 2/1996 | WIPO . |
| WO 9702357 | 1/1997 | WIPO . |

OTHER PUBLICATIONS

JPAB abstract of JP402181632A (Kaneko et al.), 1990.

Dasgupta, P.K. et al., "Electroosmosis: A Reliable Fluid Propulsion System for Flow Injection Analysis," *Anal. Chem.* 66:1792–1798 (1994).

Holloway, C.J. et al., "The analysis of amino acids and peptides by isotachophoresis," *Electrophoresis* 2:127–134 (1981).

Jacobson, S.C. et al., "Fused Quartz Substrates for Microchip Electrophoresis," *Anal. Chem.* 67:2059–2063 (1995).

Kopwillem, A. et al., "Serum Protein Fractionation by Isotachophoresis Using Amino Acids Spacers," *J. Chrom.* 118:35–46 (1976).

Manz, A. et al., "Electroosmotic pumping and electrophoretic separations for miniaturized chemical analysis systems," *J. Micromech. Microeng.* 4:257–265 (1994).

(List continued on next page.)

*Primary Examiner*—Jill Warden
*Assistant Examiner*—Alex Noguerola
*Attorney, Agent, or Firm*—Matthew B. Murphy

[57] ABSTRACT

Methods, apparatus and systems are provided for introducing large numbers of different materials into a microfluidic analytical device rapidly, efficiently and reproducibly. In particular, improved integrated pipettor chip configurations, e.g. sippers or electropipettors, are described which are capable of sampling extremely small amounts of material for which analysis is desired, transporting material into a microfluidic analytical channel network, and performing the desired analysis on the material.

88 Claims, 12 Drawing Sheets

OTHER PUBLICATIONS

Ramsey, J.M. et al., "Microfabricated chemical measurement systems," *Nature Med.* 1:1093–1096 (1995).

Seiler, K. et al., "Planar Glass Chips for Capillary Electrophoresis: Repetitive Sample Injection, Quantitation, and Separation Efficiency," *Anal. Chem.* 65:1481–1488 (1993).

Seiler, K. et al., "Electroosmotic Pumping and Valveless Control of Fluid Flow Within a Manifold of Capillaries on a Glass Chip," *Anal. Chem.* 66:3485–3491 (1994).

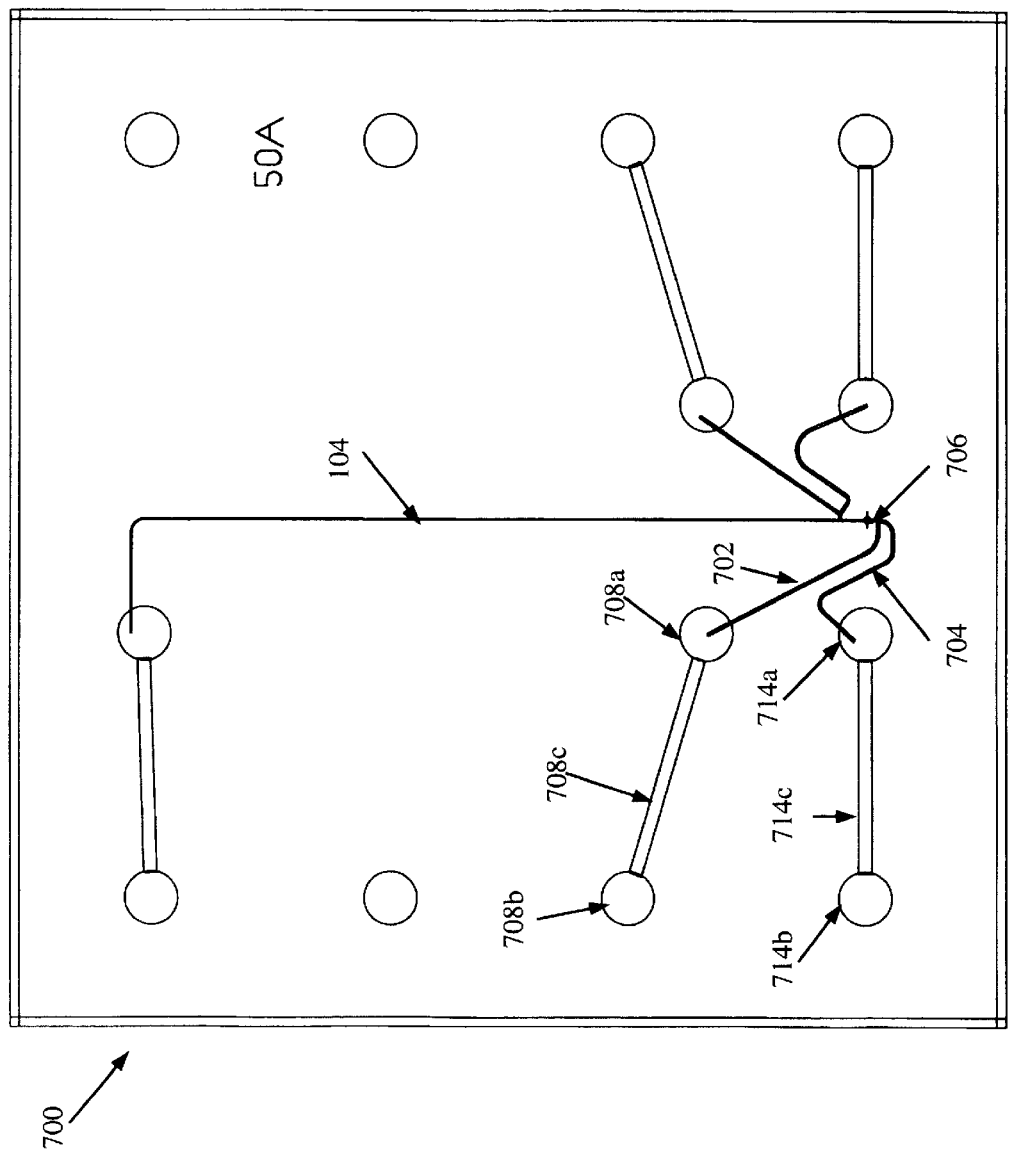

6,149,787

EXTERNAL MATERIAL ACCESSION SYSTEMS AND METHODS

BACKGROUND OF THE INVENTION

In the pharmaceutical discovery process, high-throughput screening methods and systems have been touted as one method among many, for at least initially identifying promising new pharmaceutical candidate compounds. These methods and systems have been described for use in conjunction with, or even in place of more traditional rational drug design procedures and methods.

In the past, high-throughput screening operations have simply involved the incorporation of very complex automation elements, e.g., robotics and multiplexed fluid handling systems, in order to carry out assay methods developed for use with conventional technologies, but in massively parallel experiments. Specifically, large numbers of standard assays are carried out in multi-well assay plates into which reagents are dispensed using the automated and highly parallelized fluid handling systems and robotic plate handling equipment. While such systems have increased the number of different materials that can be screened, these systems tend to be extremely complex, relatively unreliable, and have large space, reagent and cost requirements for acquiring and maintaining the overall systems.

Microfluidic devices and systems have been described as potential avenues for performing these high-throughput screening operations while minimizing the space, reagent and cost requirements of the overall systems. However, such systems have largely failed in this respect due to an inability to conveniently introduce large numbers of different reagents into the microfluidic systems. Specifically, such systems have generally relied upon conventional, large expensive fluid handling systems to introduce samples and reagents into reservoirs on microfluidic devices, effectively 'giving back' any cost or space advantages that would have been realized.

U.S. Pat. No. 5,779,868, and Published International Patent Application Nos. 98/00705 and 98/00231, on the other hand, describe microfluidic devices and systems for use in performing ultra high-throughput screening assays, which devices and systems incorporate an integrated sampling system, or "world to chip" interface, for accessing external materials and delivering them onto the device or LabChip™. These systems typically incorporate a sampling pipettor integrated into the microfluidic system for directly accessing samples, reagents and other materials from sources of such materials, e.g., compound libraries, etc. Integrated pipettor systems have generally proven very effective in rapidly, efficiently and accurately accessing large numbers of different reagents and transporting those reagents into analytical channels.

Despite the effectiveness of these integrated pipettor systems in microfluidic applications, it would generally be desirable to provide such systems with improved structural, interfacing and flow characteristics. The present invention meets these and a variety of other needs.

SUMMARY OF THE INVENTION

The present invention provides new and useful improvements to external material sampling or accession systems for microfluidic devices and systems, which provide for improved structural characteristics and improved interfacing.

In a first aspect, the invention provides methods of sampling fluids. These methods comprise dipping an open end of an open ended fluid-filled capillary element into a source of first fluid, withdrawing the capillary element from the first fluid, and permitting an amount of the first fluid remaining on the open ended capillary to spontaneously inject into the capillary channel. The capillary element is then dipped into a second fluid after a selected time period, where the selected time period is controlled to control the amount of the first fluid permitted to spontaneously inject into the open ended capillary channel.

Another aspect of the invention is a method of introducing a first fluid into a microfluidic device, comprising providing a microfluidic device having a body structure with at least first and second intersecting microscale channels disposed therein, and a capillary element extending from the body structure. The capillary element has first and second ends and a capillary channel disposed through it that is open at the first end, and in fluid communication with at least one of the first and second intersecting microscale channels in the body structure at the second end of the capillary element. The first end of the capillary channel is dipped into a source of the first fluid and then withdrawn, permitting an amount of the first fluid on the first end of the capillary channel to spontaneously inject into the capillary channel. The amount of first fluid injected into the capillary channel is transported into at least one of the first and second microscale channels that are disposed in the body structure.

In still another aspect, the present invention provides a microfluidic device that comprises a planar substrate having disposed therein an integrated channel structure that has at least first and second intersecting microscale channels included within. At least the first channel terminates in a substantially rectangular opening in the body structure. The device also includes a capillary element having a capillary channel running through it. At least one end of the capillary element is substantially rectangular. The substantially rectangular end of the capillary element is inserted into the substantially rectangular opening in the body structure and positioned such that the capillary channel in the capillary element is in fluid communication with the at least first microscale channel in the body structure.

The present invention also provides a method of joining a capillary element to a microfluidic device having an integrated channel network. The method comprises providing a microfluidic device having a body structure with at least first and second intersecting microscale channels included within, and having a substantially rectangular opening disposed in the body structure, at least one of the first and second microscale channels terminating in and being in communication with the opening. The method provides a substantially rectangular capillary element having first and second ends and a capillary channel running through the capillary element from the first end to the second end, and wherein the second end has a substantially rectangular shape. The second end of a capillary element is inserted into the opening. The capillary channel in the capillary element is positioned to be in fluid communication with the at least one of the first and second microscale channels that is in communication with the opening.

The present invention also provides a method of joining a capillary element to a microfluidic device incorporating an integrated channel network, which comprises providing first and second substrates, each having at least first planar surfaces. The first planar surface of the first substrate has at least a first microscale groove fabricated therein. Each of the first planar surfaces of the first and second substrates has a first notch fabricated in the first planar surfaces along one edge of the first and second substrates. The first planar surface of the first substrate is mated to the first planar surface of the second substrate whereby the notch in the first substrate corresponds with the notch in the first surface of the second substrate. A first end of a capillary element is inserted into an opening defined by the notch in the first and second substrates. The capillary element has a capillary channel running through the element which is placed in fluid communication with the first microscale groove when the capillary element is inserted into the opening.

Another aspect of the present invention provides a method of introducing a fluid material into a microfluidic device. The microfluidic device is comprised of a body structure which contains an integrated channel network that includes at least first and second intersecting microscale channels. At least the first channel terminates in a substantially rectangular opening in the body structure. The device also includes a capillary element having first and second ends and a capillary channel running through from the first to the second end. The second end of the capillary element is substantially rectangular. The second end of the capillary element is inserted into the substantially rectangular opening in the body structure and positioned such that the capillary channel in the capillary element is in fluid communication with the at least first microscale channel in the body structure. The first end of the capillary element is placed into a source of the fluid material. An amount of the fluid material is then drawn into the capillary channel. The amount of the fluid material is transported through the capillary channel into the at least one of the first and second microscale channels.

A further aspect of the invention is a microfluidic device comprising a body structure having at least first and second channel segments included within. The first and second channel segments each have first and second ends, where the first end of the first channel is in fluid communication with the first end of the second channel at a first fluid junction. The device includes a capillary element attached to and extending from the body structure. The capillary element comprises a capillary channel running through it, which is in fluid communication at one end with the first and second channel segments at the first fluid junction.

Another aspect of the invention is a method of introducing a first fluid material into a microfluidic system, comprising a microfluidic device, which includes a body structure having at least first and second channel segments included within. The first and second channel segments each have first and second ends. The first end of the first channel is in fluid communication with the first end of the second channel at a first fluid junction. The device also includes a capillary element attached to and extending from the body structure. The capillary element includes a capillary channel running through the element, which channel is in fluid communication at one end with the first and second channel segments at the first fluid junction. An amount of the first fluid material is introduced into the capillary channel. The amount of first fluid material is transported through the capillary channel and through the first fluid junction into the first channel segment. A second fluid material is flowed into the first channel segment from the second channel segment during the transporting step.

Another aspect of the invention is a method of transporting materials from a first microscale channel segment to a second microscale channel segment, wherein the first and second channel segments are in fluid communication at a corner having a dead zone. The method includes transporting a discrete volume of material from the first channel segment into the second channel segment around the corner. The fluid flow is simultaneously directed through the dead zone into the second channel segment from a third channel segment that is in fluid communication and collinear with the second channel segment at the corner.

Another aspect of the invention is a microfluidic device comprising a body structure having at least first, second and third channel segments included within. The first, second and third segments are in communication at a first intersection. The second and third channel segments are collinear. The third channel segment has a depth at the intersection that is less than 50% of the depth of the second channel segment.

Another aspect of the invention is a method of transporting material in a microscale channel, comprising introducing a first fluid into the channel that has a first electroosmotic mobility and a first conductivity. A second fluid is introduced into the channel, having a second electroosmotic mobility and a second conductivity. A varying voltage gradient is applied across a length of the channel to maintain a substantially constant average electroosmotic flow rate, despite a change in the total electrical resistance of the channel.

Another aspect of the invention is a microfluidic system, comprising a microfluidic device which includes a microscale channel disposed within it. The microscale channel contains varying volumes of first and second fluids, where the first and second fluids have first and second conductivities, respectively. An electrical controller is operably coupled to the microscale channel for applying a variable electric field across a length of the microscale channel. A computer is operably coupled to the electrical controller, and appropriately programmed to instruct the controller to vary the electric field to maintain a constant average electroosmotic flow rate within the channel, despite a change in total resistance across the length of the channel.

BRIEF DESCRIPTION OF THE FIGURES

FIG. 2 schematically illustrates a microfluidic device similar to that shown in FIG. 1, except employing a rectangular capillary element. The overall device is illustrated in FIG. 2A, while

FIG. 7 illustrates an actual channel layout of a microfluidic device incorporating an external sample accessing capillary as well as a sweeping channel.

DETAILED DESCRIPTION OF THE INVENTION

I. General

Figure 1:
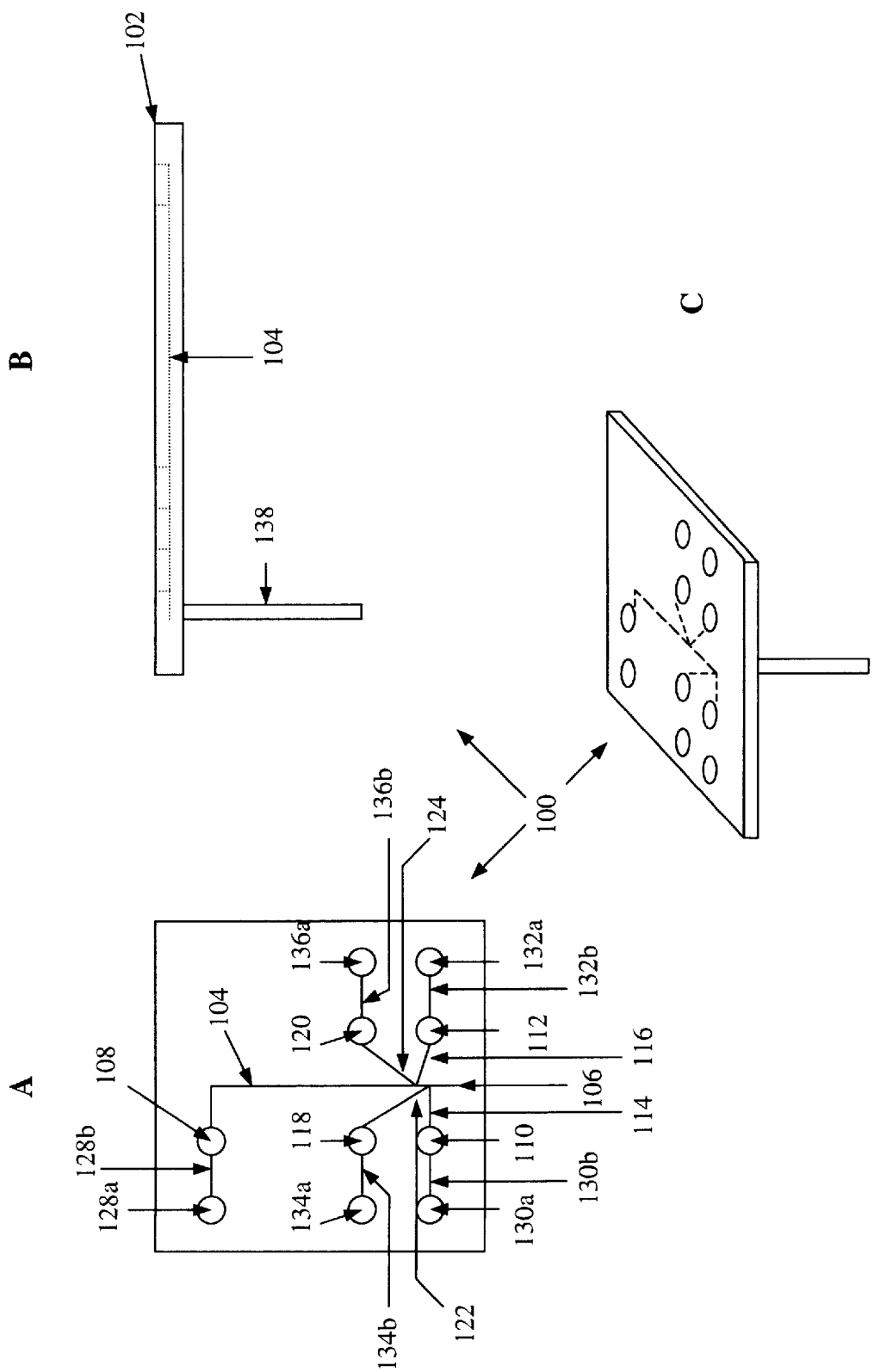
FIG. 1 schematically illustrates a microfluidic device including an external sampling capillary element, from the top (panel A), side (panel B), and perspective views (panel C).

The present invention provides methods, apparatus and systems for introducing large numbers of different materials into a microfluidic analytical device in a rapid, efficient and reproducible manner. In particular, the present invention provides improved microfluidic devices having integrated pipettor elements, e.g. sippers or electropipettors, which are capable of sampling extremely small amounts of material for which analysis is desired, transporting that material into a microfluidic analytical channel network, and performing the desired analysis on that material. The basic structure of such integrated pipettor elements is described in detail in commonly owned U.S. Pat. No. 5,779,868, and published International Patent Application No. 98/00705, each of which is incorporated herein by reference in its entirety for all purposes.

In general, such devices include an elongated body or capillary element incorporating at least one capillary channel extending the length of the capillary element. One end of the capillary channel is opened while the opposing end of the channel is in fluid communication with at least one channel that is contained within a microfluidic device. Sampling of materials is typically carried out by placing the open end of the capillary channel into contact with a source of the material to be analyzed. The material is then drawn into the capillary channel and transported into the channels of the microfluidic device. Typically, the drawing of material into the capillary, as well as the transport of the material into the channels of the microfluidic device is carried out electrokinetically. Specifically, an electric field is generally established between the source of material and some point within the microfluidic device. The electric field then causes the electrokinetic movement of the material into the capillary channel and into the microfluidic device. Optionally, however, vacuum or pressure driven forces may be applied to draw materials into the channel networks of the device.

As used herein, the term "microscale" or "microfabricated" generally refers to structural elements or features of a device which have at least one fabricated dimension in the range of from about 0.1 $\mu$m to about 500 $\mu$m. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 0.1 $\mu$m and 20 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

In many preferred aspects, the body structure of these microfluidic devices comprises at least a two-layer body structure. The bottom portion of the device typically comprises a solid substrate that is substantially planar in structure, and which has at least one substantially flat upper surface. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997 (Attorney Docket No. 17646-002610), and which is incorporated herein by reference in its entirety for all purposes.

The channels and/or chambers of the microfluidic devices are typically fabricated into the upper surface of the bottom substrate or portion, as microscale grooves or indentations, using the above described microfabrication techniques. The top portion or substrate also comprises a first planar surface, and a second surface opposite the first planar surface. In the microfluidic devices prepared in accordance with the methods described herein, the top portion also includes a plurality of apertures, holes or ports disposed therethrough, e.g., from the first planar surface to the second surface opposite the first planar surface.

The first planar surface of the top substrate is then mated, e.g., placed into contact with, and bonded to the planar surface of the bottom substrate, covering and sealing the grooves and/or indentations in the surface of the bottom substrate, to form the channels and/or chambers (i.e., the interior portion) of the device at the interface of these two components. The holes in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

In many embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

These devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices may be coupled to a sample introduction port, e.g., a pipettor, which serially introduces multiple samples into the device for analysis. Examples of such sample introduction systems are described in e.g., U.S. patent application Ser. Nos. 08/761,575 and 08/760,446 (Attorney Docket Nos. 17646-000410 and 17646-000510, respectively) each of which was filed on Dec. 6, 1996, and is hereby incorporated by reference in its entirety for all purposes.

FIG. 1 is a schematic illustration of a microfluidic device and integrated pipettor element from a top (Panel A), side (Panel B) and perspective view (Panel C). As shown, the device 100 includes a main body structure 102 that includes a channel network disposed in its interior. The channel network includes a main analysis channel 104, which fluidly connects a sample inlet 106 with waste reservoir 108. Two reagent reservoirs 110 and 112 are provided in fluid communication with the analysis channel 104 via channels 114 and 116, respectively. Reagent reservoirs 110 and 112 are paired with buffer/diluent reservoirs 118 and 120, respectively, which are in communication with channels 114 and 116 via channels 122 and 124, respectively. In order to prevent electrolytic degradation of reagent and/or buffer materials, each of reservoirs 108, 110, 112, 116 and 120 is provided in electrical and/or fluid communication with an electrical access reservoir/salt bridge channel 128*a*/*b*, 130*a*/*b*, 132*a*/*b*, 134*a*/*b*, and 136*a*/*b*, respectively. The provision of an electrical access reservoir/salt bridge allows the application of voltages via electrodes for long periods of time without resulting in substantial degradation of reagents, buffers or the like. It should be noted that as reservoir 108 is a waste well, it typically does not require a separate electrical access reservoir/salt bridge, e.g., 128*a*/*b*.

The device also includes a capillary element 138 which includes an internal capillary channel running its length, the capillary channel communicating with the analysis channel 104 via the sample inlet 106. Although shown as being perpendicular to the main body structure of the device 102, it will be appreciated that the capillary element can be coplanar with the body structure, e.g., extending in the same plane as the body structure and collinear with the analysis channel, e.g., as described in Published International Application No. WO 98/00705, which is incorporated herein by reference.

In at least one aspect, the capillary element includes at least one end that is substantially rectangular, so as to easily mate with a corresponding substantially rectangular opening on the body structure of the microfluidic device during fabrication of the overall device. Rectangular capillaries for use as the capillary element are generally commercially available, e.g., from VitroCom, Inc. or Mindrum Precision Products, Inc.

Figure 2B:
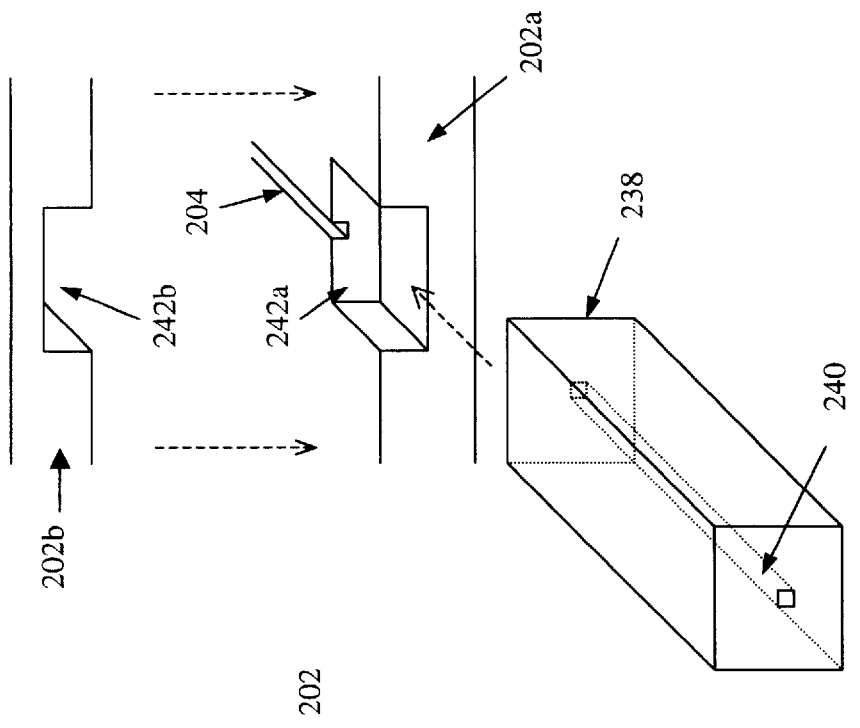
FIG. 2B illustrates an expanded view of an exemplary connection between the capillary element and the body structure of the device.
Figure 2A:
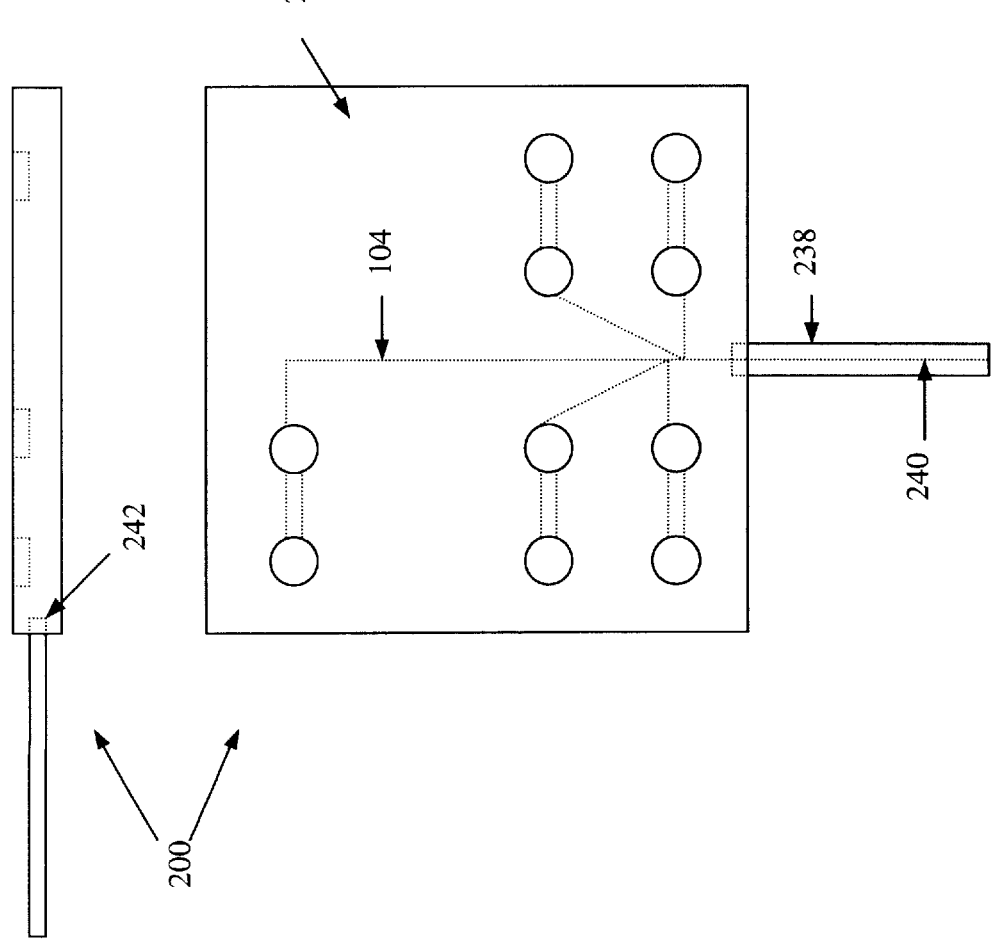

An example of a device similar to that shown in FIG. 1, but including a collinear, substantially rectangular capillary element, is shown in FIG. 2A. The same reference numerals are used for elements that are common between FIGS. 1 and 2. As shown, the overall device 100 again includes a main body structure 102 as described with reference to FIG. 1, which includes integrated channel network disposed in its interior. The rectangular capillary element 238 includes a capillary channel 240 running its length. The capillary element is attached to the body structure via a rectangular opening 242 in the body structure 102. Insertion of a rectangular end of the capillary element 238 into rectangular opening 242 places the capillary channel 240 into fluid communication with at least one of the channels in the integrated channel network within the body structure.

Because the opening 242 in the body structure is substantially rectangular, it is more conveniently fabricated than circular openings. In particular, while circular openings are typically drilled or air abraded into a body structure, rectangular openings are more conveniently fabricated by fabricating rectangular notches in two substrates by, e.g., photolithographic methods, which are mated to define the body structure of the device. The two notches are positioned to provide a single rectangular opening in the body structure. FIG. 2B illustrates an expanded view of the joining of a rectangular capillary with a two-layer microfluidic device. As shown, the device comprises a two-layer body structure including the above-described notches. As shown, the body structure 102 is made up of at least first and second planar substrates 202*a* and 202*b*, respectively. The upper surface of the lower substrate 202*a* includes grooves fabricated therein, which correspond to the desired channel structure of the finished device, e.g., groove 204. The upper substrate 202*b* is mated and bonded to the upper surface of the lower substrate 202*a* (as illustrated by the dashed arrows). Typically, bonding is carried out by thermal bonding techniques, which result in a single integrated unit having sealed channels or conduits running through its interior. The upper substrate also typically includes a number of holes disposed through it (not shown), which holes align with and provide access to the channels of the finished device. The lower and upper substrates also include notches 242a and 242b, respectively, which are aligned when the two substrates are mated, to define an opening. Although these notches could be of any shape, e.g., rectangular, hemispherical, trapezoidal, etc., it is generally easier to fabricate substantially rectangular notches, e.g., using the same fabrication techniques and steps used in fabricating the grooves/channels of the device 200, e.g., groove 204. Substantially rectangular notches produce a substantially rectangular opening along the edge of the body structure of the device. The notches generally range in depth depending upon the dimensions of the rectangular capillary element to be inserted therein. Typically, however, these notches will range in depth from about 10 μm to about 50 μm, and will be fabricated to make the transition from the channel in the capillary element to the channel in the device's body structure. For example, where a capillary element has a wall thickness of 15 μm (e.g., minor axis or interior diameter of 15 μm, with wall thickness of 15 μm yielding overall cross section of 45 μm), the notch 242a on the lower substrate 202a will typically be approximately 30 μm deep, e.g., allowing for 15 μm wall thickness and a 15 μm deep channel which matches up with the minor axis of the capillary element, while the notch 242b on the upper substrate 202b will be approximately 15 μm deep to accommodate the upper wall of the capillary element. The notches typically extend into the substrate, e.g., away from the edge, up to about 2 mm, in order to conveniently and fixedly receive the capillary element.

A substantially rectangular capillary element 238 is then inserted and attached to the body structure 202 via the opening (as shown by the dashed arrow). Typically, attachment of the capillary element is accomplished using an adhesive, e.g., epoxy, although other bonding techniques may also be used depending upon the nature of the materials used, e.g., thermal bonding, solvent welding, etc.

Although the capillary element 238 is shown as being collinear with the main analysis channel 104 of the device 200, it will be readily apparent that the rectangular capillary element can be curved or bent out of the plane of the channel network to provide a more useful sampling capillary. Bent capillaries can be held in the bent shape, e.g., by applying a rigid bent sheath, i.e., plastic sheath or a coated sheath of polyimide or Teflon (polytetrafluoroethylene) or the like, over the capillary element to hold the capillary in the bent or curved orientation. Alternatively, a rectangular capillary can extend out of the plane of the channel network, e.g., perpendicular to the channel network plane, e.g., as shown in FIG. 1. In particular, rectangular openings could be readily fabricated into the lower substrate 202a using well known fabrication techniques, e.g., etching.

As noted above, in preferred aspects, the devices described herein are typically used in conjunction with electrokinetic material transport systems. As used herein, "electrokinetic material transport systems" include systems which transport and direct materials within an interconnected channel and/or chamber containing structure, through the application of electrical fields to the materials, thereby causing material movement through and among the channels and/or chambers, i.e., positively charged species will move toward the negative electrode, while negatively charged species will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

Figure 3:
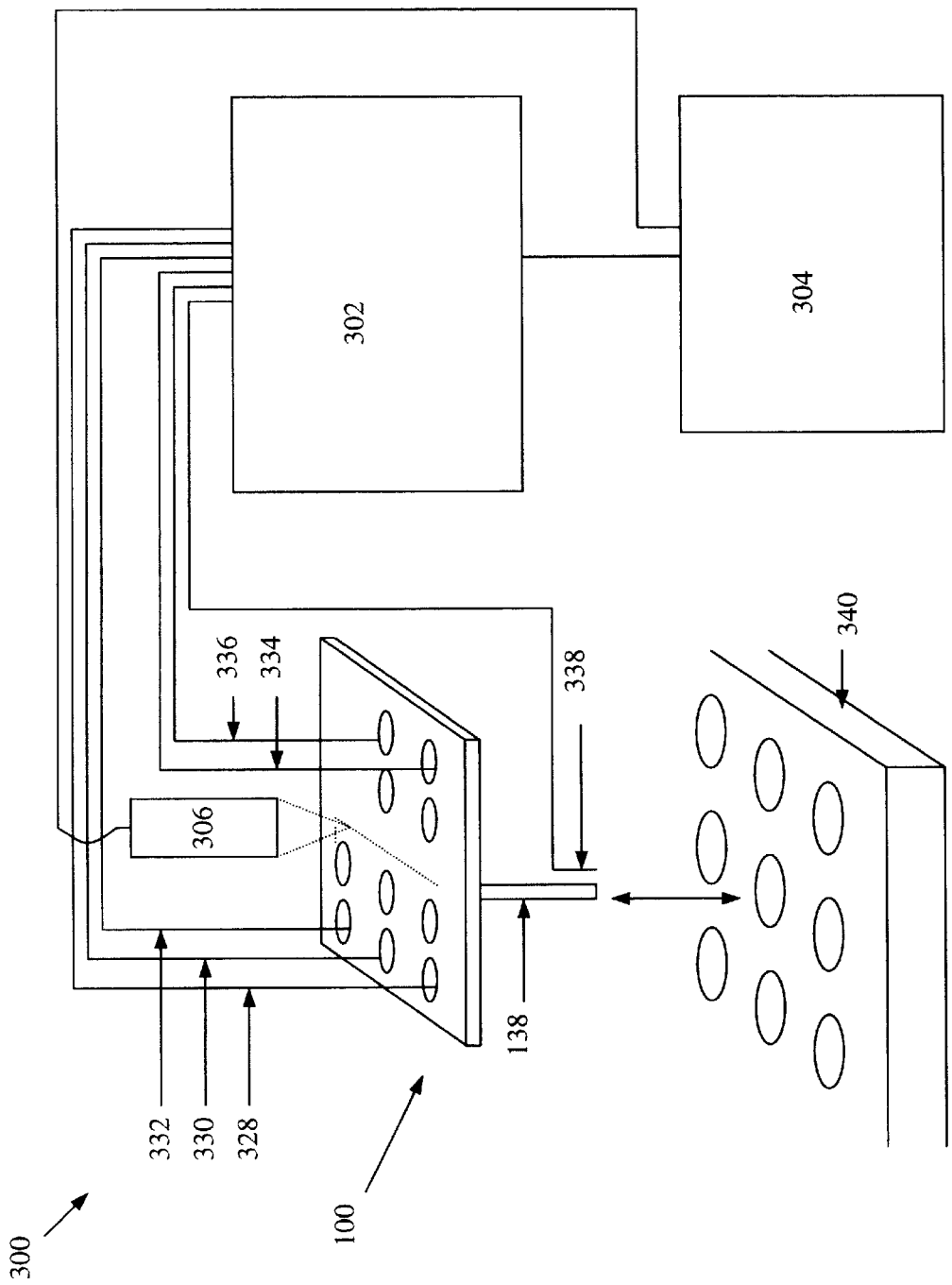
FIG. 3 illustrates an overall system including a microfluidic device, controller, detector and sample sources.

FIG. 3 is a schematic illustration of a microfluidic device incorporating an integrated pipettor element, as well as the overall material transport control and detection system, which incorporates the microfluidic device. As shown, the system 300 includes a microfluidic device 100, which incorporates an integrated pipettor/capillary element 138. Each of the electrical access reservoirs 128a–136a, has a separate electrode 328–336 disposed therein, e.g., contacting the fluid in the reservoirs. Each of the electrodes 328–336 is operably coupled to an electrical controller 302 that is capable of delivering multiple different voltages and/or currents through the various electrodes. Additional electrode 338, also operably coupled to controller 302, is positioned so as to be placed in electrical contact with the material that is to be sampled, e.g., in multiwell plate 340, when the capillary element 138 is dipped into the material. For example, electrode 338 may be an electrically conductive coating applied over capillary 138 and connected to an electrical lead which is operably coupled to controller 302. Alternatively, electrode 338 may simply include an electrode wire positioned adjacent the capillary so that it will be immersed in/contacted with the sample material along with the end of the capillary element 138. Alternatively, the electrode may be associated with the source of material, as a conductive coating on the material source well or as a conductive material from which the source well was fabricated. Establishing an electric field then simply requires contacting the electrical lead with the source well material or coating.

Figure 8:
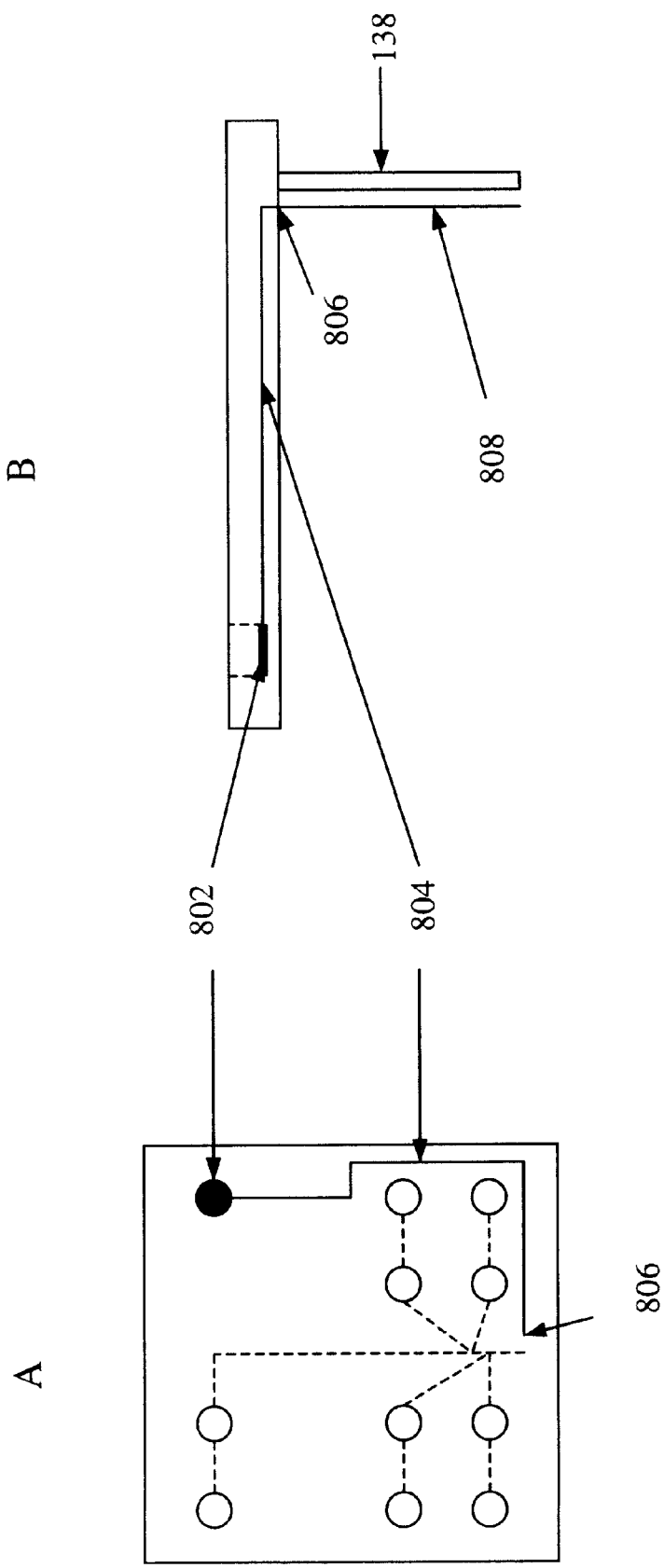
FIG. 8 illustrates a microfluidic device incorporating an integrated electrical lead for connecting an electrical controller with an electrode for use in combination with an external sample accessing capillary element in accordance the present invention.

In another alternative aspect, the electrode element that extends into the sample source is coupled to an electrical lead that is fabricated into the body structure of the microfluidic device. This lead typically includes a contact point on the upper surface of the device that permits interfacing between the controller and the electrode in the same manner as the interface between the controller and the fluid filled reservoirs of the device. The lead may extend along a channel or conduit fabricated into the device, as with the fluid channels. In certain cases, the lead exits the body structure adjacent to the external capillary element and is connected to an additional contact point, where the electrode to be contacted with the sample material may readily contact or be attached to the electrical lead. The lead extending through the body structure may simply comprise a thin wire placed into the channel prior to bonding of the substrate layers, or alternatively, may comprise a conductive fluid, polymer or metal having a low melting temperature, that is flowed into the channel, and out through an exit port adjacent to the capillary element. An illustration of this electrical lead structure is illustrated in FIG. 8 from a top (Panel A) and side (Panel B) view. In particular, a contact pad 802 is created within a reservoir-like structure in the body of the microfluidic device. An electrical conduit 804 is then provided through the body structure, e.g., within a channel-like structure that terminates in an exit port adjacent to the capillary element 138, where the lead is coupled to or integral with an electrode 806.

A processor or computer 304 is also provided operably coupled to the controller 302. The processor or computer 304 typically includes appropriate programming to instruct the controller in the delivery of appropriate voltages and/or currents to the various electrodes to carry out a given operation, e.g., moving material in accordance with a given preprogrammed protocol and/or user input instructions. The computer is also typically operably linked to a detection system 306, which is disposed in sensory communication with the analysis channel 104 in the microfluidic device 100. As used herein, "in sensory communication" refers to a detector positioned to receive a particular detectable signal from the analysis channel. For example, optical detectors that are in sensory communication with the analysis channel are typically disposed adjacent a transparent or translucent portion of the analysis channel such that the detector receives any optically detectable signal, i.e., fluorescent signal, chemiluminescent signal, chromophoric signal, or the like, from the detection window within the analysis channel. Electrochemical detectors that are in sensory communication with the analysis channel, on the other hand, typically utilize a sensor, e.g., a sensor electrode, placed into contact with he fluid within the channel. It will be readily apparent to one of ordinary skill that a variety of detection schemes may be employed within the scope of the present invention, including, optical, electrochemical, thermal, radioactive, etc. In operation, the detector detects and quantifies the signal from the analysis channel and relays the data to the processor/computer, which stores and analyzes the data relative to the operating protocol.

Once the sampled material is transported into the analysis channel of the microfluidic device, it is then subjected to the desired analysis. For example, the material may be injected into a separation channel and separated into its component parts, e.g., electrophoretically. Alternatively, in the case of diagnostic samples, e.g., patient derived, the material may be mixed with antibodies, nucleic acids or other probes, to characterize the sample. In preferred aspects, the material is mixed with components of a biochemical system that is relevant to a particular disorder, pathology or the like, and the functioning of the system is then compared in the presence and absence of the sample material to determine if the material has any pharmacologically exploitable activity, e.g., as described in WO 98/00231, incorporated herein by reference.

II. Spontaneous Injection

As noted above, the present invention relates to the accession and transport of externally stored materials into microfluidic devices using an external sampling pipettor/interface. In at least one aspect, the methods, devices and systems of the invention rely upon the phenomenon known as spontaneous injection in order to reliably, repeatedly and controllably introduce extremely small amounts of materials into microfluidic devices from external sources. As used herein, the phrase "spontaneous injection" refers to the action of fluid or other material to move into a given passage or conduit under no externally applied forces, e.g., applied pressure differentials, applied electric fields, etc. Typically, and as used herein, spontaneous injection refers to the action of fluids at the tip of a fluid-filled capillary channel in moving into the channel as a result of capillary action within the channel, surface tension on the fluid outside the channel, or the like. Thus, a fluid or other material that is "spontaneously injected" into a channel, chamber or other conduit, moves into that channel, chamber or other conduit without the assistance of an externally applied motive force.

The phenomenon of spontaneous injection is generally viewed as a problem in capillary electrophoresis applications as it presents a constant volume error in sampling (independent of sampled volume) that can vary depending upon the geometry of the capillary channel and channel tip. However, in the present invention, the characteristics of this phenomenon are exploited to provide improved sample accession methods and systems. In particular, spontaneous injection permits a number of useful advantages when sampling large numbers of different materials into microfluidic systems. For example, as noted, the rate at which materials are spontaneously injected into a capillary channel is largely dependent upon the geometry of the capillary channel and the nature of the material being sampled, e.g., the type of fluid. Thus, for a given system, spontaneous injection of sample materials is highly reproducible. Further, because spontaneous injection can be a relatively slow process, one can sample extremely small volumes of materials, depending upon the amount of time over which the material is allowed to inject. Typically, such sampled volumes range from fractions of picoliters to nanoliters.

Additional advantages of spontaneous injection systems are apparent in electrokinetically controlled systems. In particular, because spontaneous injection does not rely upon electrokinetic introduction of materials into the capillary channel, materials typically less compatible with such electrokinetic systems can be used. For example, nonaqueous materials, e.g., pharmaceutical library compounds disposed in nonaqueous solvents such as DMSO (dimethylsulfoxide), DMF (dimethylformamide), acetone, alcohols and other water soluble organic solvents, nonionic fluids or other materials, can sometimes be less suitable to electrokinetic material transport due to their nonconductive nature or extremely low conductivity. Further, because electric fields are not employed in the initial sampling process, spontaneously injected samples will not have an inherent electrophoretic biasing that can be associated with electrokinetically sampled materials, where more highly charged components of sample material are enriched for or against, by virtue of the driving electric fields.

Spontaneous injection of sample materials is also highly predictable and reproducible for a given system. In particular, appropriate modeling equations can be utilized to determine the amount of material that will be spontaneously injected over a given amount of time in any given system. Specifically, the interfacial pressure difference across a hemispherical droplet that is present at the end of a capillary channel ($\Delta P_s$), and which drives penetration or injection of the fluid into the capillary channel, is derived from the formula:

$$\Delta P_s = 2\gamma/R \tag{1}$$

where $\gamma$ is the surface tension of the fluid or buffer in the droplet and R is the radius of the droplet. For purposes of the calculation it is assumed that the droplet radius is equivalent to the outer radius of the capillary from which the droplet is suspended.

In order to determine the amount of penetration or injection of a fluid droplet into the end of the capillary channel, however, counteracting forces in the capillary channel are also considered. These include the hydrostatic pressure ($\Delta P_h$) and hydrodynamic resistance of the capillary channel, which hinder the fluid's penetration into the capillary channel. The hydrostatic pressure is calculated from:

$$\Delta P_h = \rho g h \tag{2}$$

Where $\rho$ is the density of the fluid, g is the gravitational constant, and h is the height of the fluid column. The hydrodynamic resistance of the channel is obtained from the sum of the capillary pressure ($\Delta P_{cap}$) and channel resistance ($\Delta P_{chan}$). Thus:

$$(dV/dt)(\text{Hydrodynamic Resistance}) = \Delta P_{cap} + \Delta P_{chan} \tag{3}$$

$$\Delta P_{cap} = \frac{8\eta L_1}{\pi r^4} \frac{dV}{dt} \tag{4}$$

$$\Delta P_{chan} = \frac{12\eta L_2}{WB^3} \frac{dV}{dt} \quad (\text{for } W \gg B) \tag{5}$$

In these equations, $L_1$ is the length of the capillary, r is the inner radius of the capillary $L_2$ is the length of the channel, W is the width of the channel, B is the channel depth, $\eta$ is the fluid viscosity and dV/dt is the fluid penetration flux, or the instantaneous volumetric flow rate.

Thus, the pressure balance of the system is given as follows:

$$\Delta P_s = \Delta P_h + \Delta P_{cap} + \Delta P_{chan} \tag{6}$$

Solving for the penetration flux of the fluid (dV/dt) yields the following:

$$\frac{dV}{dt} = \frac{\Delta P_s - \Delta P_h}{\text{hydrodyn. resist.}} \tag{7}$$

In which the hydrodynamic resistance is given by the equation:

$$\frac{8\eta L_1}{\pi r^4} + \frac{12\eta L_2}{WB^3} \tag{8}$$

Therefore, for any given amount of time, the penetration length, e.g., the amount of material injected can be calculated as follows:

$$\text{Penetration length} = \frac{(dv/dt)\Delta t}{\pi r^2} \quad (9)$$

From the above equation, it is apparent that one can vary the amount of material injected into a given capillary channel, i.e., having a set cross sectional area, simply by varying the amount of time over which the droplet at the end of the channel is allowed to spontaneously inject into the channel. Further, by varying the cross-sectional area of the relevant capillary channel, i.e., at the end of the capillary element, one can alter the amount of time required to inject a given volume of material.

Figure 4:
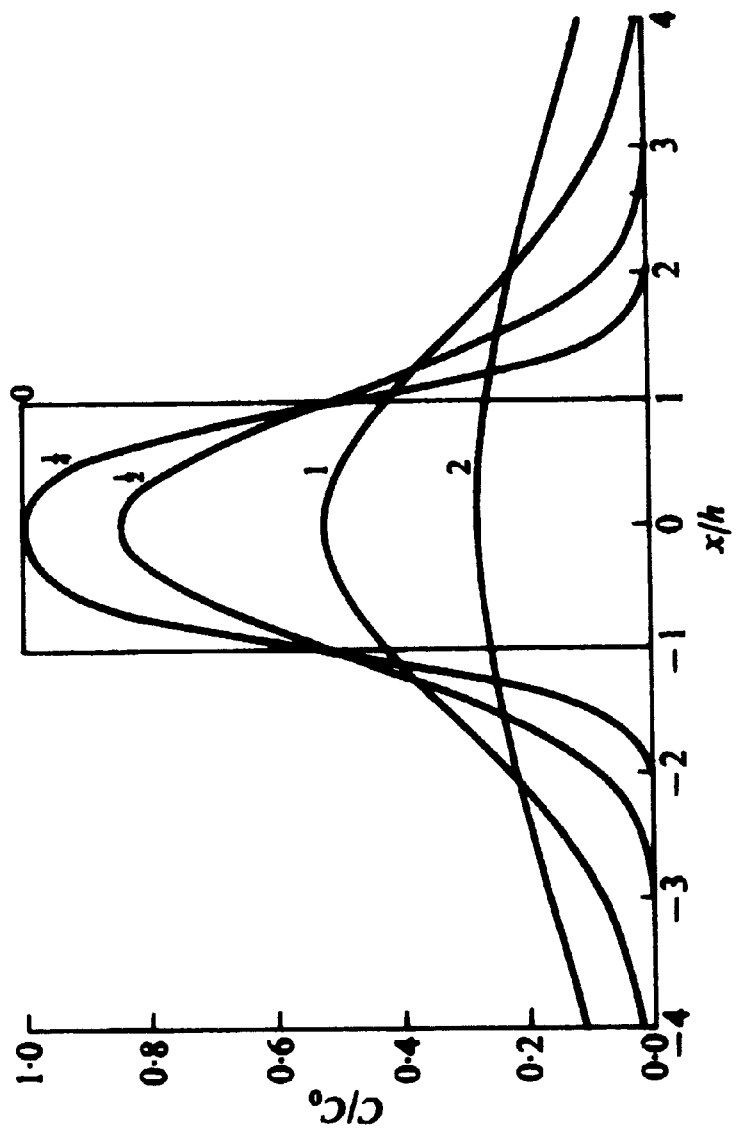
FIG. 4 is an exemplary graph showing expected diffusion kinetics of fluid material plugs in a capillary channel.

In addition to calculating and providing for precise sampling of materials, one can also predict and control a level of dilution of a sample material, which dilution results from diffusion and dispersion effects within the microscale capillary channel. In particular, the following equation approximates the dilution of a material plug within a microscale channel at time "t" relative to the concentration at time "0."

$$\frac{C_t}{C_0} = \frac{1}{2}\left[\text{erf}\frac{(h-x)}{2\sqrt{Dt}} + \text{erf}\frac{(h+x)}{2\sqrt{Dt}}\right]$$

Where $C_t$ is the concentration of the material at time 't', $C_0$ is the concentration at time '0', 'h' is the "half width" of the initial injected sample plug length at time 0 centered at x=0, x is the spatial coordinate, and 'D' is, in the most general case, a diffusion coefficient. When dispersion of the sample plug is driven by thermal diffusion, D is the molecular diffusivity (D). When dispersion is driven by a pressure driven flow in the Taylor dispersion regime, D is the Taylor diffusion coefficient ($D_t$) of the solvent in which the material to be diluted is dissolved. Although the concentration of material in the sample plug at time 't' will not be constant, e.g., concentration will be greater at the center of the plug and lower toward the edges, for purposes of this calculation, the dilution of the maximum peak height at x=0 is determined. A schematic illustration of the dilution profile or concentration-distance curves of sample plugs are illustrated in FIG. 4. The numbers on the curves are values of $(Dt/h^2)^{1/2}$. The square curve illustrates the dilution profile at time 0 (See Crank, The Mathematics of Diffusion, $2^{nd}$ Ed. (Oxford Univ. Press 1994)).

Table 1 below provides the size of a sample plug and amount of time required to produce a 1:100 dilution of the maximum peak height of a sample material ($C/C_0$=0.01) dissolved in DMSO, according to the above calculations. The calculations assume a Taylor dispersion coefficient '$D_t$' of $1\times10^{-4}$ cm$^2$/s (which is generally variable as a function of time and velocity of the fluid flow) and a molecular diffusivity "D" of $3\times10^{-6}$ cm$^2$/s.

TABLE 1

| Injection Plug Width ($\mu$m) | C/C$_0$ | Time (s) |
|---|---|---|
| 4 | 0.01 | 1.27 |
| 8 | 0.01 | 5.09 |
| 12 | 0.01 | 11.45 |
| 16 | 0.01 | 20.37 |
| 20 | 0.01 | 31.82 |
| 24 | 0.01 | 45.83 |
| 28 | 0.01 | 62.38 |

As alluded to above, the devices, methods and systems described herein are generally useful in performing a large number of different high-throughput analyses, including diagnostic assays, genomic assays, and, in particularly preferred aspects, pharmaceutical screening assays. The various types of assays that benefit from such systems and methods are generally described in Published International Patent Application Nos. 98/00231 and 98/00705, which is hereby incorporated herein by reference in its entirety for all purposes.

In particularly preferred aspects, the devices, methods and systems of the invention are particularly useful in carrying out high-throughput pharmaceutical screening assays. Typically, in such high-throughput screening operations, libraries of pharmaceutical candidate compounds are maintained dissolved or suspended in nonaqueous or organic solvents, such as DMSO, in order to keep the compounds soluble and to prevent their degradation. Pharmaceutical candidate libraries are generally compiled by a number of well known methods, including the gathering of large numbers of samples of naturally occurring materials, as well as large libraries of synthetic chemical compounds produced by, e.g., various combinatorial chemistry techniques, including focused and/or random combinatorial methods.

The various library compounds are generally transferred from the storage or 'master' plates, into separate multiwell plates (also referred to as daughter plates), and are diluted with the same organic solvent. The daughter plates are then used as the compound sources for subsequent screening assays. In particular, compounds are transferred from the daughter plates into additional multiwell plates, in which they are diluted in an appropriate assay compatible buffer, prior to subjecting them to the assay. The use of daughter plates serves to preserve the integrity of the master library plates, as well as provide for the initial dilution of the library compounds, while the subsequent plates allow further dilution of the compounds and substitution of the organic solvent with an appropriate assay compatible buffer.

As set forth above, the devices, methods and systems of the invention are readily able to sample materials in nonaqueous, e.g., organic, solvents, as well as perform in situ dilution of these materials. As such, these systems and methods are capable of sampling directly from the daughter plates, eliminating a time consuming, reagent intensive step from the currently used processes. Further, because one can relatively precisely determine dilution rates of the injected materials, one can effectively perform the dilution of the sample material or test compound, in situ, thereby eliminating yet another reagent intensive, time-consuming step.

III. Improved Flow Systems and Methods

Figure 5A:
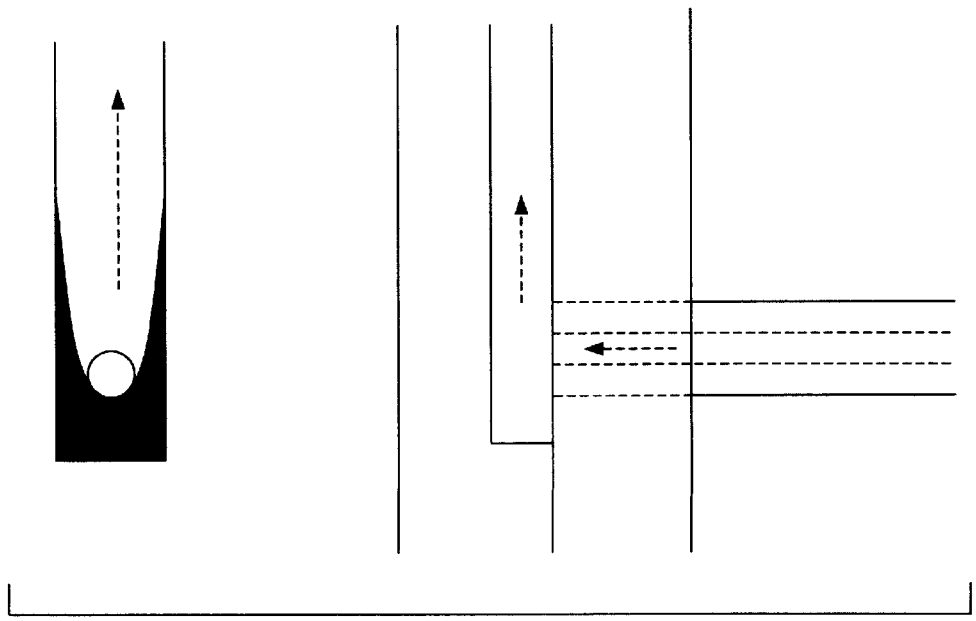
FIG. 5A illustrates flow pattern within a junction point between an external sample accessing capillary element and a microfluidic channel from top and side views.
Figure 6A:
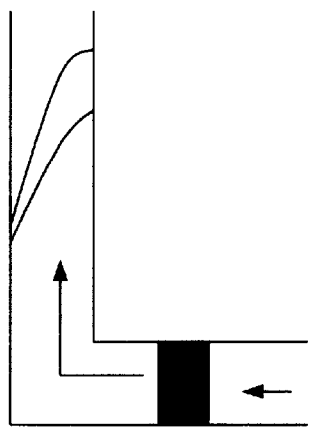
FIG. 6A illustrates sample plug distortion at a channel corner (side view).

Additional aspects of the present invention provide microfluidic devices including integrated capillary/pipettor elements and methods of using the same, which have improved flow and/or material direction characteristics. For example, in one aspect, the devices of the invention are configured so as to minimize flow-altering effects at the junction of the external capillary element and the internal channel network, e.g., resulting from dead spaces and/or sharp corners at these junctions. In particular, in those devices incorporating an external sampling capillary that extends from the plane of the body structure, e.g., as shown in FIG. 1, the junction of the capillary channel in the capillary element, with the interior channel in the body structure of the device can result in a substantial dead volume. This is illustrated from a top and side view in FIG. 5A, where the darkened region indicates a dead zone when the material is flowing in the direction of the arrows. In addition to this dead zone, this type of 'sharp corner' junction can also result in other undesirable flow characteristics, and particularly where electrokinetic transport systems are used. Specifically, as shown from a side view in FIG. 6A, a plug of material, as illustrated by the dark region (A), is electrokinetically transported up the capillary element and through the corner whereupon it is substantially deformed upon travelling through that corner, as indicated by fluid plug B. This is at least partially a result of the non-homogeneity of the electric fields passing through the corner. In particular, the material traveling through the corner at the outer edge experiences a much lower electric field than the material at the inside edge of the corner. Thus, this material at the outer edge of the corner moves slower, resulting in a "racetrack" effect at these corners, which results in a deformation of the sample material plug. This deformation substantially smears the fluid plug, and thus any signal or effect resulting from the fluid plug.

Figure 5B:
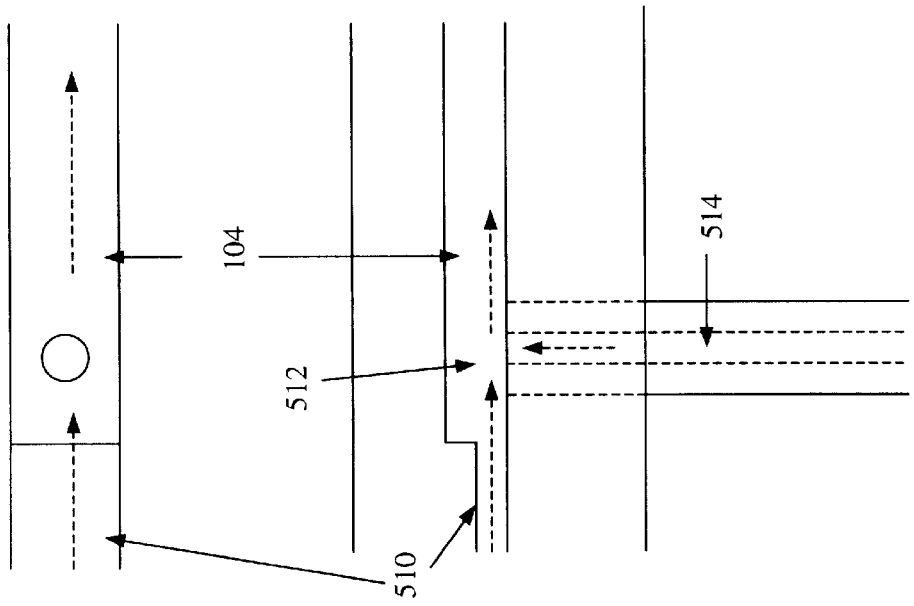
FIG. 5B illustrates flow patterns within the same junction but incorporating a sweeping channel.
Figure 6B:
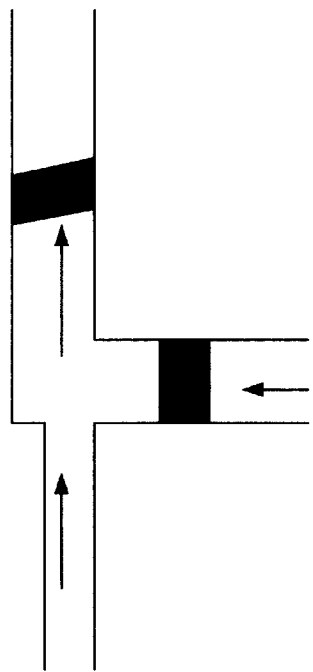
FIG. 6B illustrates the same corner incorporating a sweeping cannel showing a reduction in sample plug distortion.

In accordance with the present invention, however, a 'sweeping flow' of fluid or other material is transported through the junction point while the fluid plugs of sample material are being transported therethrough. This sweeping flow passes through what would be the dead zone, thereby preventing collection of any materials in that area, as shown in FIG. 5B. In devices that employ electrokinetic transport systems, the sweeping flow also functions to minimize the differences in the electrical fields at the inside and outside edges of a relatively sharp channel corner. In addition to these corrective effects, sweeping channels of the type described herein, also have additional advantages. This effect is shown in FIG. 6B. For example, where a particular reagent, e.g., enzyme, substrate or combination, is being introduced to the main reaction channel through the sweeping channel, its junction with the reaction channel in a collinear fashion, allows the reagent to be equilibrated across the entire width of the channel before it is mixing with a sample material, e.g., at the junction with the external capillary element.

As shown in FIGS. 5B and 6B, the sweeping flow is generally provided via an additional or "sweep" channel 510 which intersects and, at least at the junction point 512 of the analysis channel 104 and the capillary channel 514, is collinear with the main analysis channel 104. In devices employing electrokinetic transport, it is generally desirable to provide the sweep channel 510 as a shallower channel than the analysis channel 104, to reduce any pressure effects from electroosmotically transporting plugs of fluids having different ionic strengths, and thus different electroosmotic flow rates through the junction 512. The use of shallower channels to mitigate these pressure effects is described in Published International Application No. WO 98/00705, which was previously incorporated herein. Briefly, pressure effects of fluids vary as a function of the cube of the channel depth, while electroosmotic flow effects vary linearly with the channel cross-sectional area, or with the square of the channel depth. Accordingly, in preferred aspects, the sweep channel is provided with a depth that is no more than 50% of the depth of the analysis channel, preferably, no more than 20%, more preferably, no more than 10%, and in some cases as little as 1% the depth of the analysis channel at or adjacent to the junction point 512. Typically, sweep channel 510 is fabricated during the same process used to fabricate the remainder of the channel network, e.g., in the same etching process. However, because these channels have a different depth, they may require additional fabrication steps, e.g., a second etching step or process, or the like.

The sweep channel, in addition to mitigating dead zones and other undesired effects, can also be used to deliver materials needed for the given analytical operation. For example, in the case of screening assay systems, the sweep channel may be configured to deliver components of the biochemical system against which test compounds are to be screened, e.g., enzyme:substrate, ligand:receptor, cells, antibody:antigen, etc. An example of a channel network/device incorporating an integrated sweep channel configuration is shown in FIG. 7, where the device 700 comprises channels 702 and 704 which deliver reagents, e.g., from reservoirs 708a–714a, to the analysis channel 104, as well as provide a sweeping function, e.g., sweep material through the junction point 706. Reservoirs 708b–714b are provided as points of electrical access for their corresponding reagent reservoirs (708a–714a, respectively), in order to provide electrical access without causing any electrical degradation of materials in reservoirs 708a–714a, via salt bridges 708c–714c, respectively.

The improved methods and systems of the present invention, in another aspect, provide methods of transporting materials into a microfluidic system via an integrated capillary element, using a constant flow material direction system. While constant flow velocities in pressure systems are relatively simple to accomplish, a number of complications can arise in electrokinetically driven systems that include different regions of varied ionic strengths. Specifically, when sampling materials having lower ionic strengths than other fluids in the system, the material is drawn into and transported through an electrokinetically driven system faster than for higher ionic strength solutions or the remainder of the fluids in the system. For example, in certain high-throughput screening applications, a particular microfluidic channel system, e.g., collection of one or more interconnected channels, includes high ionic strength regions, also termed high salt regions, interspersed with low ionic strength or low salt regions. These varied ionic strength regions can give rise to substantial variations in flow rate through the system, e.g., when materials are being introduced, due to changes in their relative proportions throughout the system. As used herein, the terms high salt or high ionic strength and low salt or low ionic strength generally refer to the comparative conductivities of two fluids within the system.

The high ionic strength fluid regions typically approach physiological ionic strength levels, and are preferably from about 2 to about 200 times the conductivity of the low ionic strength buffer, in some cases, from about 2 to about 100 times the conductivity of the low ionic strength buffer, and more preferably, from about 2 to about 50 times the conductivity of the low ionic strength buffer, and in many cases from about 2 to about 20 or even 10 times the conductivity of the low ionic strength buffer. Typically, the high ionic strength buffer has a conductivity from about 2 millisiemens (mS) to about 20 mS, while the low ionic strength buffer has a conductivity of from about 0.1 mS to about 5 mS, provided the low ionic strength buffer has a lower conductivity than the higher ionic strength buffer.

Typically, variations from these varied ionic strength regions can be overcome, or averaged by including enough of the various regions such that any variations in velocity are minimal, e.g., an additional low ionic strength plug makes up a relatively low percentage of the overall channel length, and thus results in a very small change in the overall resistance of the channel system. However, where the different fluid regions within the channel system each occupy larger percentages of the overall channel length across which the driving electric field is applied, such variations can begin to yield adverse flow effects, i.e., speeding and slowing, which can affect detected signals from the system, etc. Additionally, in the case of screening applications, samples of material to be screened, e.g., from pharmaceutical libraries, patient samples, environmental samples, etc., may have unknown mobilities in the flowing system due to their unknown ionic strengths. Such variations again can yield variations in flow rates through such channel systems.

Accordingly, in one aspect, the present invention provides electrokinetic control of material transport/introduction into a microfluidic device, which corrects for variations in flow velocity resulting from variations among different regions of varied ionic strengths. Specifically, the present invention provides methods and systems which maintain constant velocity within a given channel by adjusting applied voltages and/or currents depending upon the proportion of the channel that is occupied by one buffer of a two buffer system, e.g., high versus low salt buffer. Because this proportion is determinable by on-line detection, e.g., by measuring the conductivity/resistance across the channel system, such methods can be carried out automatically, e.g., under computer control, with extremely short response times.

The overall electroosmotic flow velocity of a fluid in a two buffer channel system is generally given by the formula:

$$v = x\mu_1 E_1 + (1-x)\mu_2 E_2 \quad (A)$$

where v is the velocity, $\mu_1$ is the electroosmotic mobility of the first fluid, $\mu_2$ is the electroosmotic mobility of the second fluid, $E_1$ is the electric field across the first fluid region, $E_2$ is the electric field across the second fluid region, and x is the fraction of the channel that is occupied by the first fluid region, which leaves the channel fraction occupied by the second fluid region as (1−x).

Using the above equation, one can derive a relationship between the velocity, the applied voltage and the current in the channel, which can then be employed in controlling the velocities within the channel. In order to do this, there must first be determined a relationship between x, $E_1$, $E_2$ and known or measurable quantities, i.e., fluid mobility, conductivity, applied voltage ($V_{app}$), and total channel resistance ($R_{tot}$). This is started by first calculating the fill fraction of the channel as a function of $R_{tot}$ and the buffer conductivities, according to the following equation:

$$R_{tot} = (xL/A\sigma_1) + ((1-x)L/A\sigma_2) \quad (B)$$

Where $\sigma_1$ is the conductivity of the first fluid, $\sigma_2$ is the conductivity of the second fluid, and A is the channel cross-sectional area. The first operation in this equation provides the channel resistance from first fluid, while the second operation provides the channel resistance from second fluid. Solving then for x, one derives the equation:

$$x = \frac{(AR_{tot}\sigma_1/L) - \sigma_1/\sigma_2}{1 - \sigma_1/\sigma_2} \quad (C)$$

The electric fields are then calculated in terms of $V_{app}$, $R_{tot}$, the channel area and the conductivities of the buffers, as follows:

$$E_1 = V_1/(Lx) \text{ and } E_2 = V_2/(L(1-x)) \quad (D)$$

Where $V_1$ and $V_2$ are the voltage drops across the first and second fluid regions, respectively, which can be calculated from the ratio of the resistance of the particular fluid region to the total resistance of the channel:

$$V_1 = V_{app}(xL/A\sigma_1)/R_{tot} \text{ and} \quad (E)$$

$$V_2 = V_{app}[(1-x)L/A\sigma_2]/R_{tot} \quad (F)$$

Which then yields for $E_1$ and $E_2$:

$$E_1 = V_{app}/(A\sigma_1 R_{tot}) \quad (G)$$

$$E_2 = V_{app}/(A\sigma_2 R_{tot}) \quad (H)$$

Inserting these equations back into equation (A), above, and reducing, yields:

$$v = [V_{app}/L(\sigma_2 - \sigma_1)][\mu_1(\sigma_2 - L/AR_{tot}) - \mu_2(\sigma_1 - L/R_{tot})] \quad (I)$$

This velocity equals the initial velocity $V_{init}$, which is the velocity when the system is entirely filled by the first fluid, e.g., a baseline level of flow:

$$v_{init} = \mu 1(V_0/L) \quad (J)$$

where $V_0$ is the initial applied voltage. Accordingly, in order to keep the velocity constant, e.g., by keeping it equal to the initial velocity, the voltage applied to the system can be implied by:

$$V_{app} = \frac{V_0(\sigma_2 - \sigma_1)}{[(\sigma_2 - L/AR_{tot})] - [(\mu_2/\mu_1)(\sigma_1 - L/AR_{tot})]} \quad (K)$$

Of course, variations in cross-sectional area between one channel and another in a system, e.g., an internal channel and an external capillary element, can result in variations from this equation. However, such variations are minimized by selecting these channels to have similar cross sectional areas. Alternatively, one can factor in variations in channel cross section, across the system.

Considering the above-described relationships, it can thus be seen that by monitoring variations in conductivity/resistance within a channel or channel system, knowing the channel dimensions, and applied voltages, one can vary the applied voltages to correct for variations in flow rates within a microfluidic channel system despite variations in the overall conductivity/resistance across the length of the channel which variations result from changes in the portion of the system that contains a higher conductivity fluid versus a lower conductivity fluid. In accordance with the methods and systems described herein, the resistance/conductivity of the channel or channel system is determined to instruct the appropriate variation in applied voltages, e.g., in accordance with the relationships set out above. Because preferred systems employ electrokinetic material transport systems, the appropriate interfaces and instrumentation are quite easily put in place for carrying out these flow control methods. Specifically, electrical measurements, e.g., resistance/conductivity, are easily made through the same system of electrodes and power supplies that are used to control electrokinetic transport.

Further, these relationships are also used to program a computer or other processor to automatically vary the applied voltages depending upon the measured resistance/conductivity of the system, and user input values, i.e., channel dimensions, in order to maintain a constant flow rate within the channel system.

The present invention is further illustrated by the following non-limiting examples.

EXAMPLES

Example 1

Spontaneous Injection

The efficacy of spontaneous injection was demonstrated in a microfluidic device having a 1 cm channel with a reservoir at one end and being coupled to a 3 cm external capillary element at the other end. 50 mM HEPES, pH 7.5 was the buffer used for the experiment. 50 $\mu$M EDANS was used as a fluorescent sample material to determine the efficacy of the spontaneous injection technique.

Figure 9:
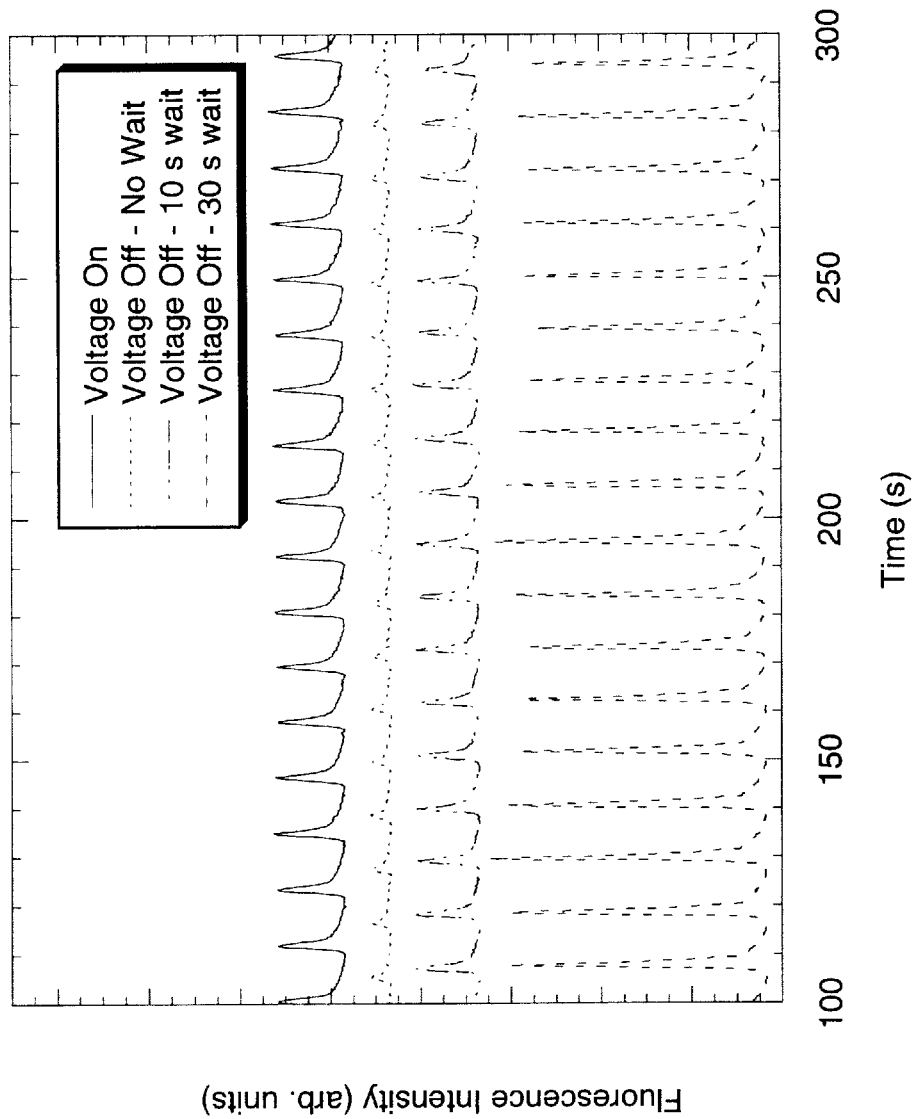
FIG. 9 is a plot of fluorescent intensity of fluorescent sample material plugs that were either electrokinetically or spontaneously injected into a microfluidic device.

In the experiment, the end of the capillary element was contacted with the buffer well of a multiwell plate, then moved into contact with a sample well (containing the fluorescent material), followed by contact with another buffer well. For comparison, the injections were run using either electrokinetic injection or spontaneous injection. For electrokinetic injection, during the injection process, a voltage of 2250 V was applied between the wells of the multiwell plate and the reservoir at the other end of the fluid channel. For spontaneous injection, the voltage was turned off when the capillary was placed into contact with the sample material well, and turned back on in the buffer wells. The amount of material spontaneously injected was varied by varying the amount of time the capillary was contacted to the sample material. The contact time was either 0.9 seconds ("no wait," as it takes 0.9 seconds to move the capillary element), 10 seconds and 30 seconds. FIG. 9 illustrates a comparative plot of fluorescent intensity of sample material plugs injected using electrokinetic injection ("Voltage On") and three different lengths of spontaneous injection ("Voltage Off-No Wait," "Voltage Off-10s wait," and "Voltage Off-30s wait"). As can be seen from the plot, spontaneous injection with a 10 second contact time gave approximately the same size injection as the electrokinetically injected plugs, while the 30 second spontaneous injection gave a significantly larger injection.

Example 2

Sweeping Flow

Several microfluidic devices having integrated capillary elements as shown in FIG. 7 were prepared, etched to 1.5 µm in side/sweeping channel and 15 µm in main channel depths. A 20-µm inner diameter capillary was attached to each planar device (not shown in FIG. 7). Three devices randomly selected from the same fabrication lot were tested for the effects of joint sweeping on the broadness of the injected peaks. In all devices tested, the use of joint sweeping noticeably reduced the tailing of the injected peaks.

For the peak injection experiments, a buffer containing 50 mM HEPES at pH 7.5 was used as the running buffer. The dye solution contained the running buffer with 50-µM EDANS dye was used as an exemplary sample material in order to monitor peak width within the main channel. All devices tested were first treated with 1 N NaOH for 20 to 30 minutes then rinsed with de-ionized water thoroughly twice before all the wells and channels were filled with the HEPES buffer. On the multiwell plate, a series of three wells containing buffer, buffer, and dye solutions, respectively, were set up for the peak injection measurements. The dwell times were chosen to be: running buffer=20s, pre-guard buffer (same as running buffer, but from different plate well)=0.5s, sample (dye solution)=0.5s, post-guard buffer (again, same as running buffer but from a different plate well)=0.5s.

Figure 10A:
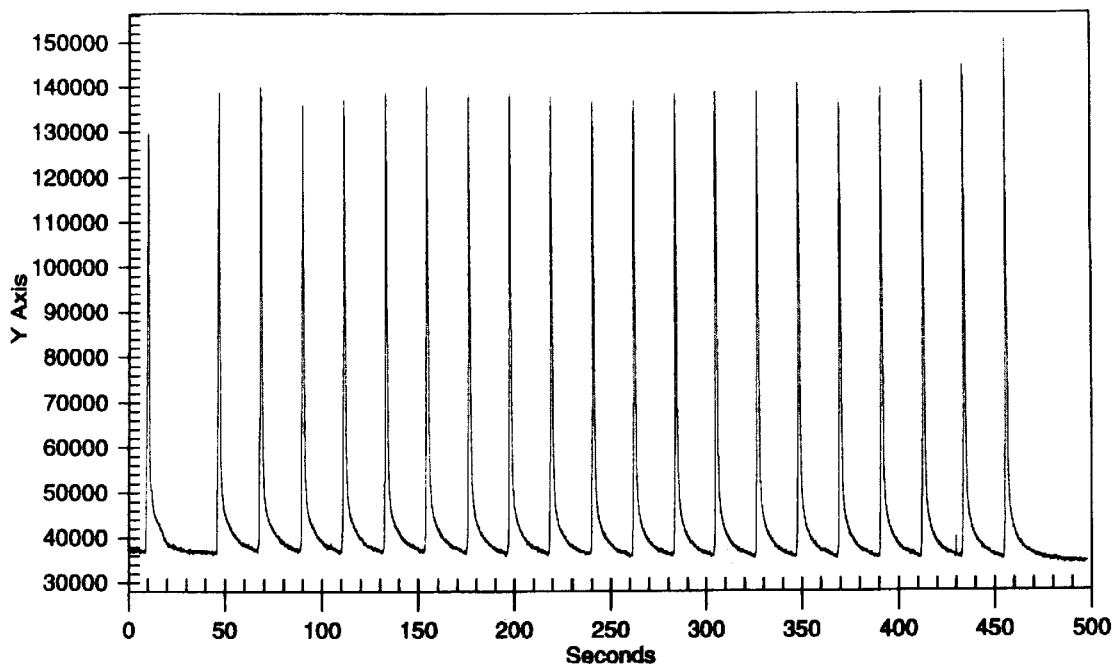
FIGS. 10a–f show peak width data for injections made into a microfluidic channel both with and without sweeping flow from an integrated sweeping channel.
Figure 10B:
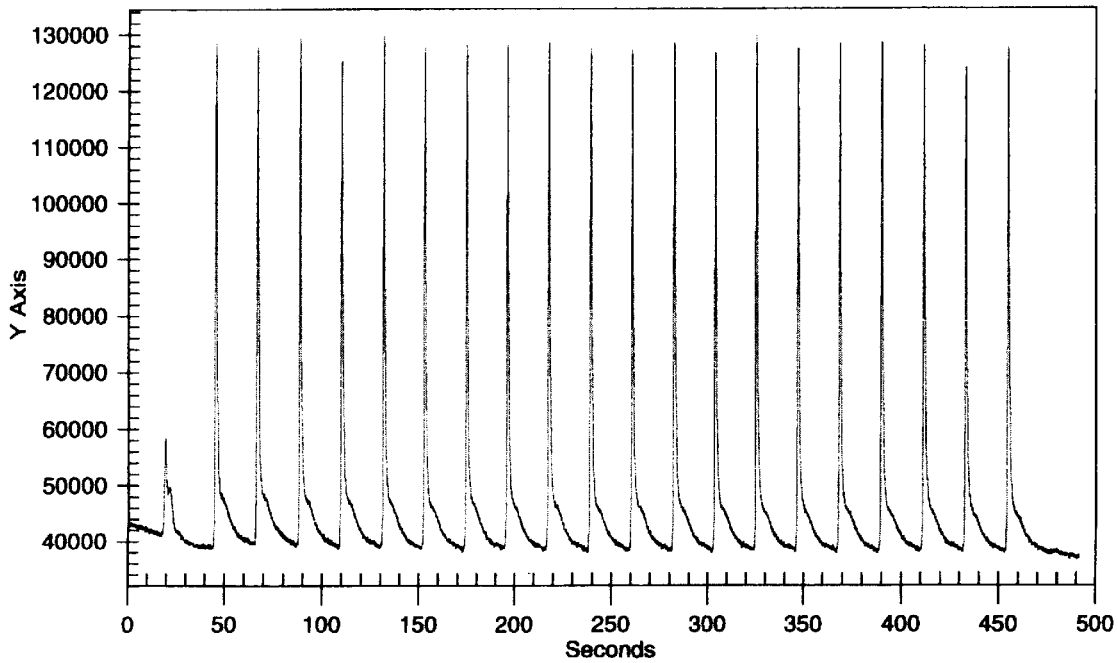

FIGS. 10a and 10b illustrate one set of injection peak data with and without joint sweeping. FIG. 10a shows the peak injection data using a sweeping current of 0.5 µA each from wells 712a and 714a. The voltage at the waste well 716a and capillary electrode (not shown) were set at 100 V and 2500 V, respectively. The total main channel 104 current was 5.74 µA. FIG. 10b shows the control experiment without a sweeping current from wells 712a and 714a. A current of 0.5 µA each from the non-sweeping side channels from wells 708a and 710a was used to keep the total current, thus total flow rate, in the main channel constant. As can be seen clearly in the data, tailing in the injection peaks in FIG. 10b is noticeably reduced with a modest sweeping current (17% of the total flow).

Figure 10C:
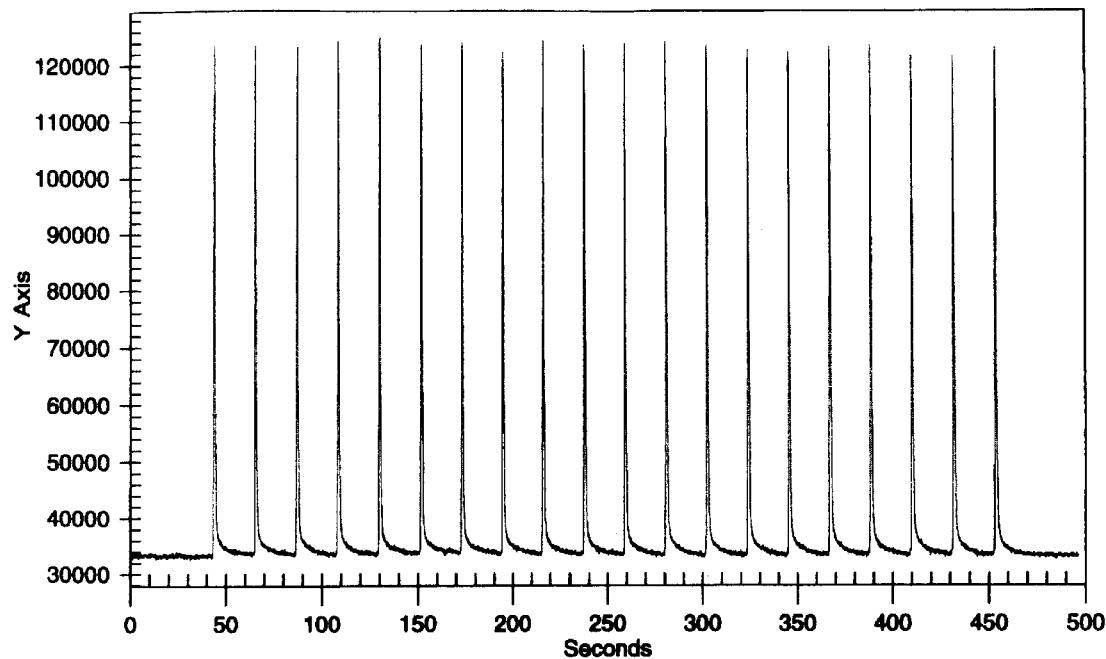
Figure 10D:
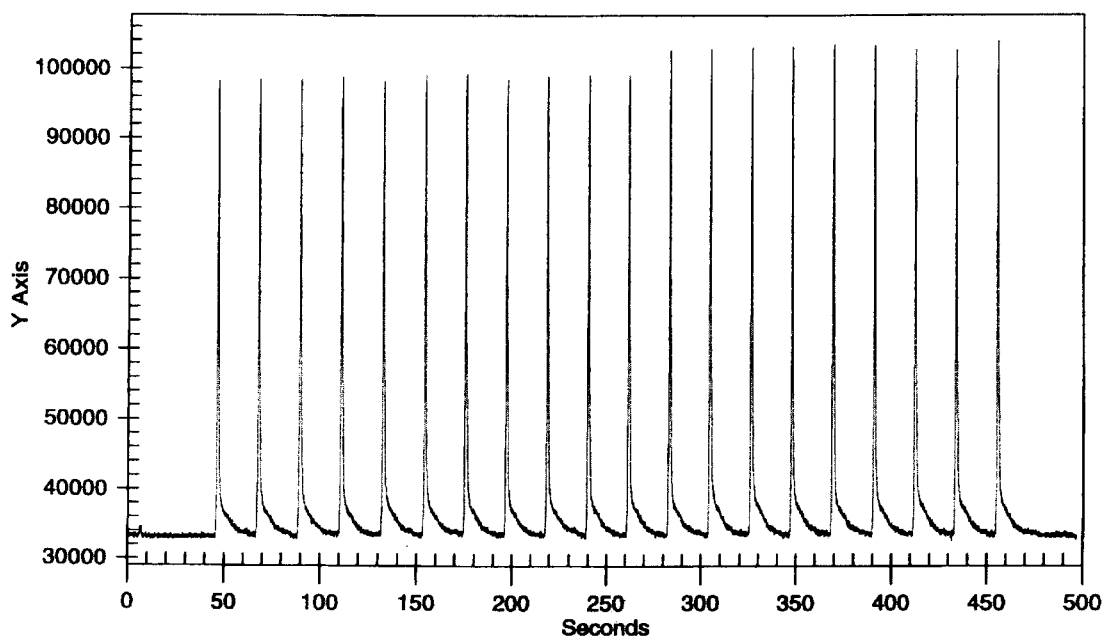
Figure 10E:
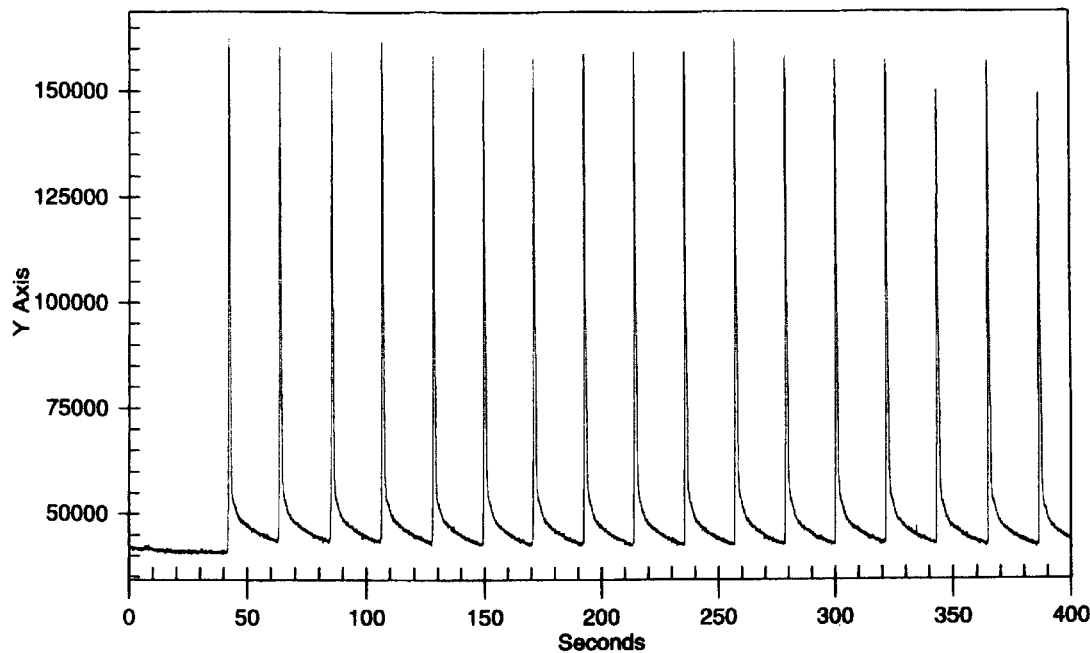
Figure 10F:
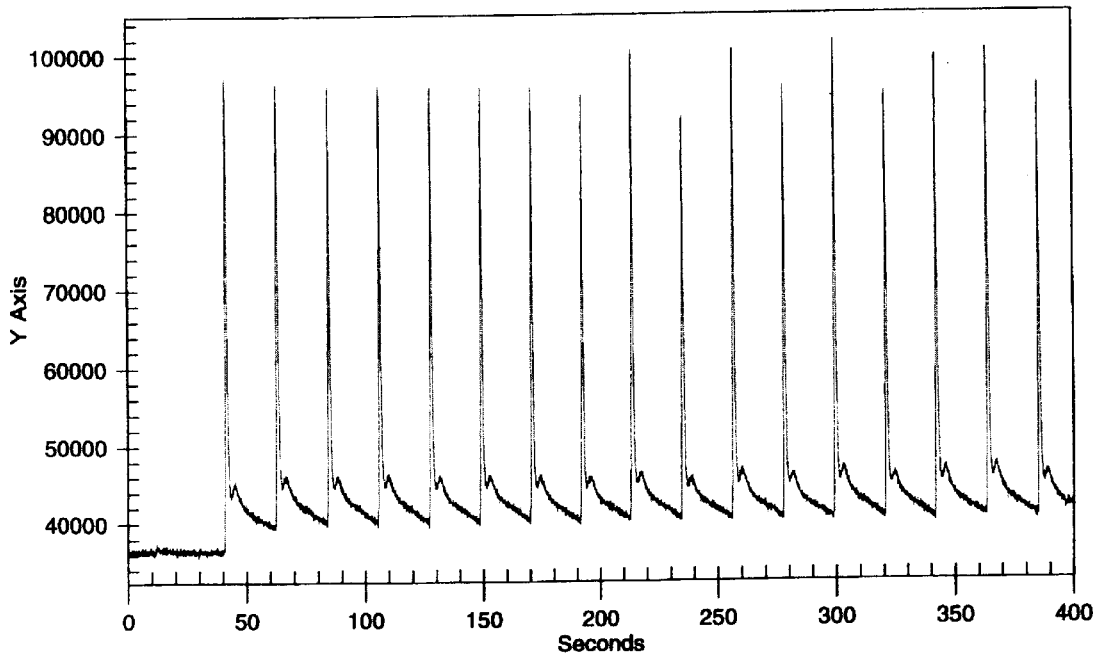

FIGS. 10c and 10d illustrate the effects of joint sweeping for a second device. In FIG. 10c, a sweeping current of 2 µA each from wells 712a and 714a was used to achieve narrow injection peaks with very little tailing. Other voltage settings were similar to the experiments used in FIGS. 10a and b. The control experiment, FIGS. 10d, with 2 µA each from wells 708a and 710a, clearly shows more tailing in the injection peak. Results of testing of a third device, using same experimental parameters as in FIGS. 10c and d, are shown in FIGS. 10e and 10f. Again, FIG. 10e is the injection run using joint sweeping and FIG. 10f with no joint sweeping. In this case, the injection peaks without sweeping show a secondary peak at the tail end, and joint sweep was able to remove these secondary peaks.

As can be seen from the above experiments, the use of an integrated sweeping channel was able to yield a significant reduction in the dispersion due to the capillary-to-channel joint in the injection peaks. Typically, the higher the sweeping flow, the better the reduction in the dispersion.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of sampling fluid, comprising:
   (a) dipping an open end of an open ended capillary element comprising a capillary channel disposed therethrough, into a source of second fluid the capillary channel being filled with a first fluid;
   (b) withdrawing the capillary element from the second fluid;
   (c) permitting an amount of the second fluid remaining on the open ended capillary to spontaneously inject into the capillary channel;
   (d) dipping the capillary element into a third fluid after a first selected time period, the first selected time period being controlled to control the amount of the first fluid permitted to spontaneously inject into the open ended capillary channel.

2. The method of claim 1, further comprising:
   dipping the open end of the capillary element into a source of a fourth fluid after dipping the capillary into the source of third fluid;
   withdrawing the capillary from the fourth fluid;
   permitting an amount of the fourth fluid remaining on the open ended capillary element to spontaneously inject into the capillary channel;
   dipping the capillary into the third fluid after a second selected time period, the second selected time period being controlled to control the amount of the fourth fluid permitted to spontaneously inject into the open ended capillary channel.

3. The method of claim 1, further comprising transporting the amount of second fluid through the capillary channel for a second selected time, the second selected time being selected to control an amount of dilution of the amount of second fluid.

4. The method of claim 3, wherein the second selected time is controlled by controlling a flow rate of the amount of the second fluid through the capillary channel.

5. The method of claim 3, wherein the second selected time is controlled by selecting at least one of a length or a diameter of the capillary channel.

6. The method of claim 1, wherein the step of tansporting the second fluid material through the capillary channel comprises applying an electric field along a length of the capillary channel to electrokinetically transport the second fluid material through the capillary channel.

7. The method of claim 1, further comprising introducing an amount of a low salt buffer into the capillary channel before injecting the second fluid material into the capillary channel.

8. The method of claim 1, further comprising introducing an amount of low salt buffer fluid into the capillary channel after injecting the amount of second fluid material into the capillary channel.

9. The method of claim 1, further comprising introducing an amount of a high salt buffer into the capillary channel before injecting the second fluid material into the capillary channel.

10. The method of claim 1, further comprising introducing an amount of high salt buffer fluid into the capillary channel after injecting the amount of second fluid material into the capillary channel.

11. The method of claim 1, wherein the second fluid material comprises a first test compound.

12. The method of claim 1, further comprising repeating steps (a)–(d) with a plurality of separate fluid sources, each of the separate fluid sources comprising a different test compound.

13. The method of claim 1, wherein the plurality of different fluid sources comprises at least 1000 separate fluid sources, each separate fluid source comprising a different test compound.

14. The method of claim 1, wherein the second fluid comprises a nonaqueous fluid.

15. The method of claim 14, wherein the nonaqueous fluid comprises DMSO, DMF, acetone or an alcohol.

16. The method of claim 14, wherein the amount of second fluid injected into the capillary channel is less than 1 $\mu$l.

17. The method of claim 14, wherein the amount of second fluid injected into the capillary channel is less than 100 nl.

18. The method of claim 14, wherein the amount of second fluid injected into the capillary channel is less than 10 nl.

19. The method of claim 14, wherein the amount of second fluid injected into the capillary channel is less than 1 nl.

20. The method of claim 14, wherein the amount of second fluid injected into the capillary channel is between 0.1 pl and 100 nl.

21. The method of claim 14, wherein the capillary channel has a cross sectional area of between about 10 $\mu m^2$ and $1 \times 10^5$ $\mu m^2$, and the first selected time is less than 30 seconds.

22. The method of claim 21, wherein the first selected time is less than about 10 seconds.

23. The method of claim 21, wherein the first selected time is less than about 5 seconds.

24. The method of claim 21, wherein the first selected time is less than or equal to about 1 second.

25. The method of claim 1, wherein the capillary channel is in fluid communication with at least a first microscale channel disposed in a body structure, and the second fluid is transported through the capillary channel and into the first microscale channel.

26. The method of claim 25, wherein the first microscale channel is intersected by and in fluid communication with at least a second microscale channel disposed in the body structure.

27. The method of claim 26, further comprising:

flowing a component of a biochemical system into the first microscale channel from the second microscale channel whereby the second fluid contacts the component of the biochemical system; and detecting an effect of the second fluid on the component of the biochemical system.

28. The method of claim 1, further comprising introducing first and second high salt fluid regions into the capillary channel before and after, respectively, the amount of second fluid injected into the capillary channel.

29. The method of claim 28, further comprising introducing first and second low salt fluid regions into the capillary channel before the first high salt fluid region and after the second high salt fluid region, respectively.

30. A method of introducing a first fluid into a microfluidic device, comprising:

providing a microfluidic device having a body structure with at least first and second intersecting microscale channels disposed therein, and a capillary element extending from the body structure, the capillary element having first and second ends and a capillary channel disposed therethrough the capillary channel being open at the first end, and in fluid communication with at least one of the first and second intersecting microscale channels in the body structure at the second end of the capillary element;

dipping the first end of the capillary channel into a source of the first fluid;

withdrawing the first end of the capillary channel from the source of first fluid;

permitting an amount of the first fluid on the first end of the capillary channel to spontaneously inject into the capillary channel; and transporting the amount of first fluid injected into the capillary channel into the at least one of the first and second microscale channels disposed in the body structure.

31. The method of claim 30, wherein the transporting step is carried out by applying an electric field along a length of the capillary channel to electrokinetically transport the amount of first fluid through the capillary channel and into the at least one of the first and second microscale channels.

32. The method of claim 30, further comprising introducing a high salt fluid region into the capillary channel before or after the first fluid is injected into the capillary channel.

33. The method of claim 30, further comprising introducing a high salt fluid region into the capillary channel before and after the first fluid is injected into the capillary channel.

34. The method of claim 30, further comprising introducing a low salt fluid region into the capillary channel before or after the first fluid is injected into the capillary channel.

35. The method of claim 30, further comprising introducing a low salt fluid region into the capillary channel before and after the first fluid is injected into the capillary channel.

36. The method of claim 30, further comprising introducing first and second high salt fluid regions before and after respectively, the amount of first fluid injected into the capillary channel.

37. The method of claim 36, further comprising introducing a first low salt fluid region before the first high salt fluid region, and a second low salt fluid region after the second high salt fluid region.

38. The method of claim 30, wherein the first fluid comprises a first test compound.

39. The method of claim 30, further comprising repeating the dipping, withdrawing, permitting and transporting steps with a plurality of separate fluid sources, each of the separate fluid sources comprising a different test compound.

40. A microfluidic device, comprising:
- a body structure having disposed therein an integrated channel structure that includes at least first and second intersecting microscale channels, at least the first channel terminating in a substantially rectangular opening in the body structure;
- a capillary element having a capillary channel disposed therethrough, and at least one end of the capillary element that is substantially rectangular, the substantially rectangular end of the capillary element being inserted into the substantially rectangular opening in the body structure and positioned such that the capillary channel in the capillary element is in fluid communication with at least first microscale channel in the body structure.

41. The microfluidic device of claim 40, wherein the body structure comprises:
- a first planar substrate having a first surface having a plurality of intersecting grooves fabricated thereon, and at least a first substantially rectangular notch fabricated into the surface along one edge of the substrate, at least one of the plurality of grooves terminating in the first notch;
- a second planar substrate comprising a first surface having a second substantially rectangular notch fabricated in the first surface of the second substrate along an edge of the second substrate, the first surface of the second planar substrate overlaying the first surface of the first planar substrate whereby the second notch and the first notch form the substantially rectangular opening in the body structure.

42. The microfluidic device of claim 41, wherein the capillary element is substantially coplanar with the first and second planar substrates.

43. The microfluidic device of claim 41, wherein the capillary channel in the capillary element comprises a cross-sectional area that is approximately equal to a cross sectional area of the at least first microscale channel in the body structure.

44. The microfluidic device of claim 41, wherein the capillary element comprises a curved portion that is not coplanar with the first and second planar substrates.

45. The microfluidic device of claim 41, wherein the capillary element comprises a sheath disposed over an outer surface of the capillary element.

46. The microfluidic device of claim 41, wherein the sheath is selected from plastic, polyimide and polytetrafluoroethylene.

47. The microfluidic device of claim 41, wherein the capillary element is fixedly inserted into the opening.

48. The microfluidic device of claim 41, wherein at least one of the capillary element, and the body structure comprises a solid substrate material selected from a polymeric substrate, a silica based substrate and a ceramic substrate.

49. The microfluidic device of claim 48, wherein each of the capillary element and the body structure comprise a polymeric solid substrate material.

50. The microfluidic device of claim 48, wherein each of the capillary element and the body structure comprise a silica based solid substrate material.

51. The microfluidic device of claim 50, wherein the silica-based substrate is selected from glass, quartz, fused silica and silicon.

52. A method of joining a capillary element to a microfluidic device having an integrated channel network disposed therein, comprising:
- providing a microfluidic device having a body structure with at least first and second intersecting microscale channels disposed therein, and having a substantially rectangular opening disposed in the body structure, at least one of the first and second microscale channel terminating in and being in communication with the opening;
- providing a substantially rectangular capillary element having first and second ends and a capillary channel disposed through the capillary element from the first end to the second end, and wherein the second end has a substantially rectangular shape; and
- inserting the second end of a capillary element into the opening, the capillary channel in the capillary element being positioned to be in fluid communication with the at least one of the first and second microscale channels that is in communication with the opening.

53. A method of joining a capillary element to a microfluidic device incorporating an integrated channel network, comprising:
- providing first and second substrates each having at least first planar surfaces, the first planar surface of the first substrate having at least a first microscale groove fabricated therein, and each of the first planar surfaces of the first and second substrates having a first notch fabricated in the first planar surfaces along one edge of the first and second substrates;
- mating the first planar surface of the first substrate to the first planar surface of the second substrate whereby the notch in the first substrate corresponds with the notch in the first surface of the second substrate;
- inserting a first end of a capillary element into an opening defined by the notch in the first and second substrates, the capillary element having a capillary channel disposed therethrough, the capillary channel being placed in fluid communication with the first microscale groove when the capillary element is inserted into the opening.

54. The method of claim 53, wherein the first microscale groove in the surface of the first substrate and the notch in the surface of each of the first and second substrates are etched into the surface.

55. A method of introducing a fluid material into a microfluidic device, comprising:
- providing a microfluidic device, comprising:
  - a body structure having disposed therein an integrated channel network that includes at least first and second intersecting microscale channels, at least the first channel terminating in a substantially rectangular opening in the body structure;
  - a capillary element having first and second ends and a capillary channel disposed therethrough from the first to the second end, the second end of the capillary element being substantially rectangular, the second end of the capillary element being inserted into the substantially rectangular opening in the body structure and positioned such that the capillary channel in the capillary element is in fluid communication with at least first microscale channel in the body structure;
- placing the first end of the capillary element into a source of the fluid material;
- drawing an amount of the fluid material into the capillary channel;

transporting the amount of the fluid material through the capillary channel into the at least one of the first and second microscale channels.

56. The method of claim 55, wherein the drawing and transporting steps comprise applying an electric field between the first end of the capillary channel and integrated channel network in the body structure to move the first fluid into and through the capillary channel electrokinetically.

57. A microfluidic device comprising:
   a body structure having at least first and second channel segments disposed therein, the first and second channel segments each having first and second ends, the first end of the first channel being in fluid communication with the first end of the second channel at a first fluid junction; and
   a capillary element attached to and extending from the body structure, the capillary element comprising a capillary channel disposed therethrough, the capillary channel being in fluid communication at one end with the first and second channel segments at the first fluid junction.

58. The microfluidic device of claim 57, wherein the capillary channel meets and is in fluid communication with the first channel segment at an angle between 45° and 90°.

59. The method of claim 58, wherein the body structure comprises a plurality of intersecting channels arranged in a first plane, and wherein the capillary element extends out of the first plane at an angle between about 45° and 90°.

60. The microfluidic device of claim 57, wherein a portion of the first channel segment that is adjacent to and in fluid communication with the first fluid junction is collinear with a portion of the second channel segment that is adjacent to and in fluid communication with the first fluid junction.

61. The microfluidic device of claim 57, wherein the second channel segment comprises a first cross-sectional dimension substantially equivalent to a first cross-sectional dimension of the first channel segment and a second cross sectional dimension less than one half of a second cross sectional dimension of the first channel segment.

62. The microfluidic device of claim 61, wherein the second cross-sectional dimension of the second channel segment is no greater than one tenth the second cross sectional dimension of the first channel segment.

63. The microfluidic device of claim 57, wherein the second end of the second channel segment is in fluid communication with a fluid source of at least a first component of a biochemical system.

64. The microfluidic device of claim 57, wherein the second end of the first channel segment is in fluid communication with a waste reservoir.

65. The microfluidic device of claim 57, wherein the second ends of the first and second channel segments are in fluid communication with first and second reservoirs, respectively, the first and second reservoirs being disposed in the body structure.

66. The microfluidic device of claim 57, comprising at least first and second electrodes disposed in electrical contact with a fluid in the first and second reservoirs, respectively.

67. The microfluidic device of claim 66, wherein the at least first component of the biochemical system produces a detectable signal indicative of a relative level of functioning of the biochemical system.

68. The microfluidic device of claim 57, further comprising a material transport system for transporting a first material through the capillary channel into the first channel segment and for concomitantly directing a flow of a second material from the second channel segment through the first fluid junction into the first channel segment.

69. The microfluidic device of claim 57, wherein the body structure comprises;
   a first substrate having at least a first planar surface, the first planar surface having first and second groove segments disposed thereon;
   a second substrate having a first planar surface, the first planar surface of the second substrate being mated with the first planar surface of the first substrate, the first and second groove segments defining the first and second channel segments.

70. The microfluidic device of claim 69, wherein the capillary element is attached to the body structure and the capillary channel is in fluid communication with the first fluid junction via an opening disposed through the body structure.

71. The microfluidic device of claim 70, wherein the opening disposed through the body structure comprises an opening disposed through at least one of the first and second substrates, the capillary element being fixedly inserted into the opening.

72. The microfluidic device of claim 70, wherein the opening in the body structure comprises a third groove segment disposed in the first surface of the first substrate and having first and second ends, the first end of the third groove segment terminating at one end at a first edge of the first planar surface of the first substrate and defining a third channel segment having first and second ends in the body structure, the first end of the third channel segment defining an opening in a first edge of the body structure, and the second end of the third channel segment being in fluid communication with the first fluid junction.

73. The microfluidic device of claim 72, wherein the capillary element is attached to the body structure at the first edge of the body structure and wherein the capillary channel is in fluid communication with the third channel segment.

74. A method of introducing a first fluid material into a microfluidic system, comprising:
   providing a microfluidic device comprising:
      a body structure having at least first and second channel segments disposed therein, the first and second channel segments each having first and second ends, the first end of the first channel being in fluid communication with the first end of the second channel at a first fluid junction; and
      a capillary element attached to and extending from the body structure, the capillary element comprising a capillary channel disposed therethrough, the capillary channel being in fluid communication at one end with the first and second channel segments at the first fluid junction;
   introducing an amount of the first fluid material into the capillary channel;
   transporting the amount of first fluid material through the capillary channel and through the first fluid junction into the first channel segment; and
   flowing a second fluid material into the first channel segment from the second channel segment during the transporting step.

75. The method of claim 74, wherein the second fluid material comprises at least a first component of a biochemical system.

76. The method of claim 75, wherein the component of a biochemical system produces a detectable signal indicative of a relative functioning of the biochemical system.

77. The method of claim 76, wherein the first fluid material comprises a test compound, and further comprising detecting the relative functioning of the biochemical system in the presence and absence of the test compound.

78. The method of claim 75, wherein the at least first component of the biochemical system comprises a mixture of an enzyme and its substrate.

79. The method of claim 75, wherein the at least first component of the biochemical system comprises two members of a specific binding pair.

80. The method of claim 79, wherein the specific binding pair comprises a receptor and a ligand that specifically binds the receptor.

81. The method of claim 79, wherein the specific binding pair comprises an antibody and an antigen specifically bound by the antibody.

82. The method of claim 74, wherein the introducing step further comprises introducing a region of spacer fluid into the capillary channel before and after the amount of first fluid material introduced into the capillary channel.

83. The method of claim 82, wherein the spacer fluid region comprises a low salt buffer.

84. The method of claim 82, wherein the spacer fluid region comprises a high salt zone and a low salt zone, the high salt zone being adjacent to the amount of first fluid material in the capillary channel.

85. A method of transporting materials from a first microscale channel segment to a second microscale channel segment, wherein the first and second channel segments are in fluid communication at a corner having a dead zone, comprising:

transporting a discrete volume of material from the first channel segment into the second channel segment around the corner;

simultaneously directing a flow of fluid through the dead zone into the second channel segment from a third channel segment that is in fluid communication and collinear with the second channel segment at the corner.

86. A microfluidic device, comprising a body structure having at least first, second and third channel segments disposed therein, the first, second and third segments in communication at a first intersection, the second and third channel segments being collinear, and the third channel segment having a depth at the intersection that is less than 50% a depth of the second channel segment.

87. The microfluidic device of claim 86, wherein the second and third channel segments are disposed within a primary plane of a planar body structure and wherein the first channel segment comprises a capillary element extending out of the plane of the planar body structure.

88. The microfluidic device of claim 87, wherein the capillary element extends out of the plane of the planar body structure at an angle of between about 45° and 90°.

* * * * *

UNITED STATES PATENT AND TRADEMARK OFFICE
CERTIFICATE OF CORRECTION

PATENT NO : 6,149,787
DATED : November 21, 2000
INVENTOR(S) : Chow et al.

It is certified that error appears in the above-identified patent and that said Letters Patent are hereby corrected as shown below:

Column 23, line 4, please delete "tansporting" and insert --transporting--.
Column 26, line 8, please delete "channel" and insert --channels--.

Signed and Sealed this

First Day of May, 2001

Attest:

NICHOLAS P. GODICI

Attesting Officer    Acting Director of the United States Patent and Trademark Office